(12) United States Patent
Dhar et al.

(10) Patent No.: US 7,973,148 B2
(45) Date of Patent: Jul. 5, 2011

(54) CRUSTACEAN EXPRESSION VECTOR

(75) Inventors: Arun K. Dhar, Sykesville, MD (US); F. C. Thomas Allnutt, Glenwood, MD (US)

(73) Assignee: Advanced Bionutrition Corporation, Columbia, MD (US)

( * ) Notice: Subject to any disclaimer, the term of this patent is extended or adjusted under 35 U.S.C. 154(b) by 321 days.

(21) Appl. No.: 11/587,770

(22) PCT Filed: Apr. 15, 2005

(86) PCT No.: PCT/US2005/012979
§ 371 (c)(1),
(2), (4) Date: Jun. 5, 2007

(87) PCT Pub. No.: WO2005/102041
PCT Pub. Date: Nov. 3, 2005

(65) Prior Publication Data
US 2007/0292952 A1 Dec. 20, 2007

Related U.S. Application Data

(60) Provisional application No. 60/562,459, filed on Apr. 15, 2004.

(51) Int. Cl.
*C07H 21/02* (2006.01)
*C07H 21/04* (2006.01)
*A01N 63/00* (2006.01)
*A01N 65/00* (2009.01)
*A61K 48/00* (2006.01)
*C12N 5/00* (2006.01)
*C12N 5/02* (2006.01)

(52) U.S. Cl. ............... 536/23.1; 536/24.1; 424/93.2; 424/93.21; 424/93.7; 435/325

(58) Field of Classification Search .............. 536/23.1
See application file for complete search history.

(56) References Cited

U.S. PATENT DOCUMENTS

| 5,217,879 | A  | 6/1993  | Huang et al. |
| 7,396,548 | B2 | 7/2008  | Kyle |
| 2004/0047881 | A1 | 3/2004  | Kyle et al. |
| 2004/0081638 | A1 | 4/2004  | Kyle et al. |
| 2004/0177392 | A1 | 9/2004  | Barratt et al. |
| 2006/0120999 | A1 | 6/2006  | Dhar et al. |
| 2006/0121468 | A1 | 6/2006  | Allnutt et al. |
| 2006/0127453 | A1 | 6/2006  | Harel et al. |
| 2006/0130162 | A1 | 6/2006  | Kyle et al. |
| 2006/0258623 | A1 | 11/2006 | Harel et al. |
| 2006/0265766 | A1 | 11/2006 | Kyle et al. |
| 2007/0082008 | A1 | 4/2007  | Harel et al. |

FOREIGN PATENT DOCUMENTS

| EP | 1369481 | 12/2003 |
| WO | WO 00/75288 | 12/2000 |
| WO | WO 02/12522 | 2/2002 |
| WO | WO 03/048325 | 6/2003 |

OTHER PUBLICATIONS

Wilson, Je et al., Naturallu occurring dicistronic cricket paralysis virus RNA is regulated by two internal ribosomal entry sites, Mol. Cell. Biol., 2000, 20:49990-4999.*
Arenal, A et al, 2000, Biotechnologica Aplicada, 17:247-250).*
Liu, W-J et al., 2005, Virology, 334:327-341.*
Cervallos and Sarnow, 2005, Journal of Virology, 79:677-683).*
Christian, P. D. and Scotti, P. D. (1998). Picorna-like viruses of insects. In: Miller LK, Andrew Ball K (eds) The Insect Viruses, New York, Plenum Press, pp. 301-329.
Kim J. M., Vanguri S., Boeke J. D., Gabriel A., Voytas D. F. (1998). Transposable elements and genome organization: a comprehensive survey of retrotransposons revealed by the complete *Saccharomyces cerevisiae* genome sequence. *Genome Res.* 8: 464-78.
Lightner, D.V. (1996). Epizootiology, distribution and the impact on international trade of two penaeid shrimp viruses in the Americas. Rev. Sci. Tech. Off. Int. Epiz. 15: 579-601.
Ruckert, R. R. (1996). Picornaviridae: the viruses and their replication. In: Field Virology, B. N. Fields, D. N. Knipe, and P. M. Howley (ed.), Lippincott-Raven, Philadelphia, PA, pp. 609654.
Tu C, Huang H-T, Chuang S-H, Hsu J-P, Kuo S-T, Li N-J, Hsu T-L, Li M-C, Lin S-Y (1999) Taura syndrome in Pacific white shrimp *Penaeus vannamei* cultured in Taiwan. Dis Aquat Org 38: 159-161.
Lightner, D. V., Redman, R. M., Poulos, B. T., Nunan, L. M., Mari, J. L., and Hasson, K. W. (1996). Risk of spread of penaeid shrimp viruses in the Americas by the international movement of live and frozen shrimp. Rev. Sci. Tech. Off. Int. Epiz. 16: 146-160.
Bonami Jr, Hasson KW, Mari J, Poulos BT, Lightner DV (1997) Taura syndrome of marine penaeid shrimp: characterization of the viral agent. J Gen Virol 78: 313-319.
Dhar, A. K., Roux, M. R. and Klimpel, K. R. 2002. Quantitative assay for measuring the load of Taura syndrome virus (TSV) and yellow head virus (YHV) in shrimp by real-time RT-PCR using SYBR Green chemistry. Journal of Virological Methods 104: 69-82.
Kidwell M. G., and Lisch D. (1997) Transposable elements as sources of variation in animals and plants. *Proc. Natl. Acad. Sci. USA* 94: 7704-11.
Kumar, A. and Hirochika, H. (2001). Applications of retrotransposons as genetic tools in plant biology. *Trend Plant Biol*. 6: 127-134.
Evgen'EV, et al. 1997. Penelope, a new family of transposable elements and its possible role in hybrid dysgenesis in *Drosophila virilis*. Proc. Natl. Acad. Sci. U.S.A. 94: 196-201.

(Continued)

*Primary Examiner* — Valarie Bertoglio
(74) *Attorney, Agent, or Firm* — Marianne Fuierer; Moore & Van Allen, PLLC

(57) ABSTRACT

Methods and constructs for genetic manipulation of one or more of shrimp, shellfish, mollusks, and fish are disclosed. The nucleic acid construct includes a promoter and an internal ribosome entry site of an insect picomavirus, such as a cricket paralysis-like picomavirus. One or more open reading frames can be operably associated with one or both of the promoter and the internal ribosome entry site, and one or more proteins or protein subunits can be expressed upon introduction of the construct into a host cell, such as into a shrimp. Method for producing immortalized crustacean cell lines using enhancer elements derived from shrimp and/or shrimp viruses are also described.

40 Claims, 21 Drawing Sheets

OTHER PUBLICATIONS

Li, W-H., Gu, Z., Wang, H., and Nekrutenko, A. (2001) Evolutionary analyses of the human genome. *Nature* 409: 847-9.

Mari, J., Poulos, B. T., Lightner, D. V. and Bonami, J. R. (2002). Shrimp Taura syndrome virus: economic characterization and similarity with members of the genus Cricket paralysis-like viruses. J. Gen. Virol. 83: 915-926.

Mark, H., Goldbach, R. W., Vlak, J. M., and van Hulten, M. C. W. (2004). Genetic variation among isolates of *White Spot Syndrome Virus*. Arch. Virol. 149: 673-697.

Matz MV et al. (1999) Fluorescent proteins from nonbioluminescent *Anthozoa* species. Nat Biotechnol 17:969-97.

Moore, N. F., Kearns, A. and Pullin, J. S. K. (1980). Characterization of cricket paralysis virus-induced polypeptides in *Drosophila* cells. J. Virol. 33: 1-9.

Moore, N. F., Reavy, B. and Pullin, J. S. K. (1981). Processing of cricket paralysis virus-induced polypeptides in *Drosophila* cells: production of high molecular weight polypeptides by treatment with iodoacetamide. Arch. Virol. 68: 1-8.

Pimpinelli, S., Berloco, M., Fanti, L., Dimitri, P., Bonaccorsi, S., Marchetti, E., Caizzi, R., Caggese, C., and Gatti, M. (1995) Transposable elements are stable structural components of *Drosophila melanogaster* heterochromatin. *Proc. Natl. Acad. Sci. U S A.* 92: 3804-8.

Plasterk, R. H. A., Izsvak, Z., and Ivies, Z. (1999). Resident aliens: the Tcl/mariner superfamily of transposable elements. *Trends Genet*. 15: 326-332.

Pyatkov, K. I., Shostak, N. G., Zelentsova, E. S., Lyozin, G. T., Melekhin, M. I., Finnegan, D. J., Kidwell, M. G., and Evgen'ev, M. B. 2002. *Penelope* retroelements from *Drosophila virilis are* active after transformation of *Drosophiola melanogater*. Proc. Natl. Acad. Sci. 99: 16150-16155.

Robles-Sikisaka, R., Garcia, D. K., Klimpel, K. R. and Dhar, A. K. (2001). Nucleotide sequence of 3'-end of the genome of Taura syndrome virus of shrimp suggests that it is related to insect picornaviruses. Arch. Virol.146: 941-952.

Roux, M, Pain, A., Klimpel, K. R. and Dhar, A. K. 2002. The Liposaccharide and 13-1, 3 glucan binding gene is unregulated in white spot virus (WSV) infected shrimp (*Penaeus stylirostris*). Journal of Virology 76: 7140-7149.

SanMiguel, P, Tikhonov, A, Jin, Y. K., Motchoulskaia, N., Zakharov, D., Melake-Berhan, A., Springer, P. S., Edwards, K. J., Lee, M., Avramova, Z., Bennetzen, J. L. (1996) Nested retrotransposons in the intergenic regions of the maize genome. *Science* 274: 765-68.

Smit, A. F. (1999) Interspersed repeats and other mementos of transposable elements in mammalian genomes. *Curr. Opin. Genet. Dev.* 9: 657-63.

Sasaki, J. and Nakashima, N. (1999). Translation initiation at the CUU codon is mediated by the internal ribosomal entry site of an insect picorna-like virus in vitro. J. Virol. 73: 1219-1226.

Sasaki, J., Nakashima, N., Saito, H. and Noda, H. (1998). An insect picoma-like virus, *Plautia stali* intestine virus, has genes of capsid proteins in the 3' part of the genome. Virology 244: 50-58.

Van Hulten, M. C. W., Tsai, M-F., Schipper, C. A., Lo, C-F., Kou, G-H., and Valk, J. M. (2000). Analysis of a genomic segment of white spot syndrome virus of shrimp containing ribonucleotide reductase genes and repeat regions. J. Gen. Virol. 81: 307-316.

Van Hulten, M. C. W., Witteveldt, J., Peters S., Kloosterboer, N., Tarchini, R., Fiers, M., Sandbrink, S., Lankhorst, R. K., and Valk, J. M. 2001a. The white spot syndrome virus DNA genome sequence. Virology 286: 7-22.

Van Hulten, M. C. W., and Valk, J. M. 2001b. Identification and phylogeny of a protein kinase gene of white spot syndrome virus. Virus Genes 22: 201-207.

Wilson, J. E., Powell, M. J., Hoover, S. E. and Sarnow, P. (2000). Naturally occurring dicistronic cricket paralysis virus RNA is regulated by two internal ribosomal entry sites. Mol. Cell. Biol. 20: 49990-4999.

Xu, Z., Dhar, A. K., Wyrzykowski, J. and Alcivar-Warren, A. 1999. Identification of abundant and informative microsatellites from shrimp (*Penaeus monodon*) genome. Animal Genetics 30:1-7.

Yang, F., He, J., Lin, X., Li, Q., Pan, D., Zhang, X., and Xu, X. 2001. Complete genome sequence of the shrimp white spot bacilliform virus. J. Virol. 75:11811-11820.

Shike, H; Dhar, AK; Burns, JC.; Shimizu, C.; Jousset, FX,; Klimpel, KR., and Bergoin, M. 2000. Infectious hypodermal and hematopoietic necrosis virsu (IHHNV) of shrimp is related to mosquito brevidensoviruses. Virology, 277: 167-177.

Domier, LL., et al. 2003 In vivo activity of Phopalosiphum padi rirus internal ribosome entry sites, J of Gen. Virology vol. 84; No. 2, pp. 415-419.

Woolaway Ke, et al. 2001 The 5' untranslated region of Rhopalosiphum Padi Virus contains an Internal Ribosome entry site, J of Virology, vol. 75, No. 21, pp. 10244-10249.

Shibuya, N, et al. 2003 Conditional rather than absolute requirements of the capsid coding sequence for initiaition of methionine-independent translation in *Plautia stali* intestine virus, J of Virology, vol. 77, No. 22, pp. 12002-12010.

Morgan, Ra,; Couture, L., Elroy-Stein, O.; Ragheb, J.; Moss, B., and Anderson, W.; 1992 Retroviral vectors containing putative internal ribosome entry sites; development of a polycistronic gene transfer system and application to human gene therapy, Nucleic Acids Research, vol. 20. No. 6, pp. 1293-1299.

Hellen, C.; Sarnow, P.; 2001 Internal ribosome entry sites in eukaryotic mRNA molecules, Genes & Development, vol. 15, pp. 1593-1612.

Martinex-Salas, E., and Fernandez-Miragall, O., 2004, Picornavirus IRES: Structure Function Relationship, Current Pharm Design, vol. 10, pp. 3757-3767.

\* cited by examiner

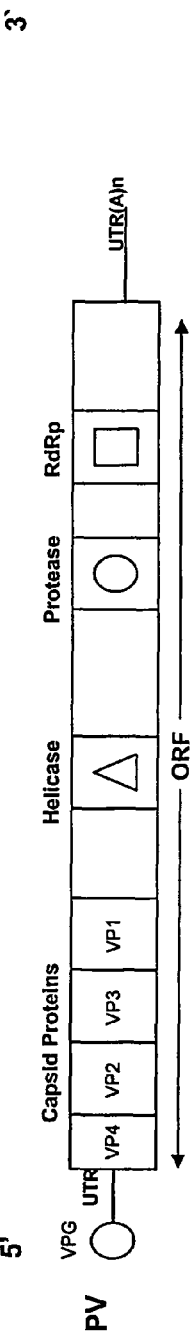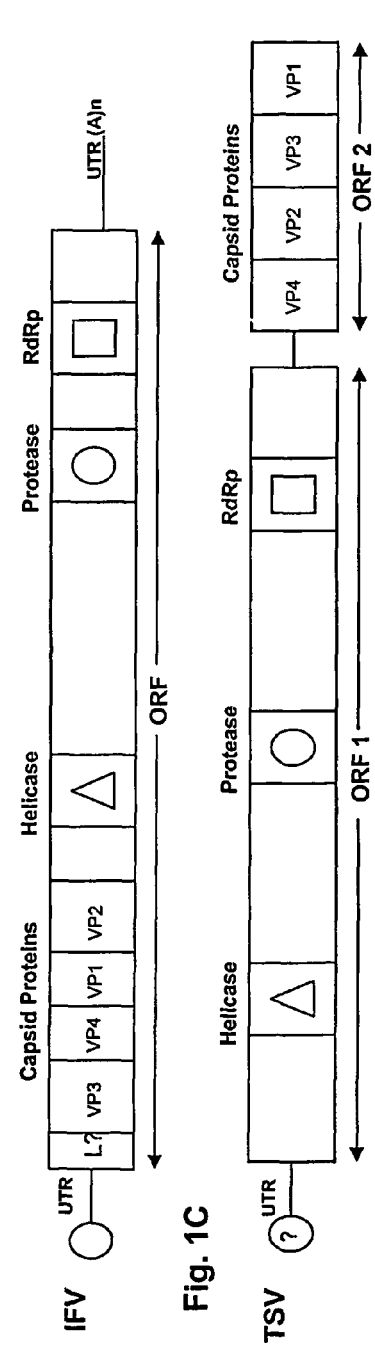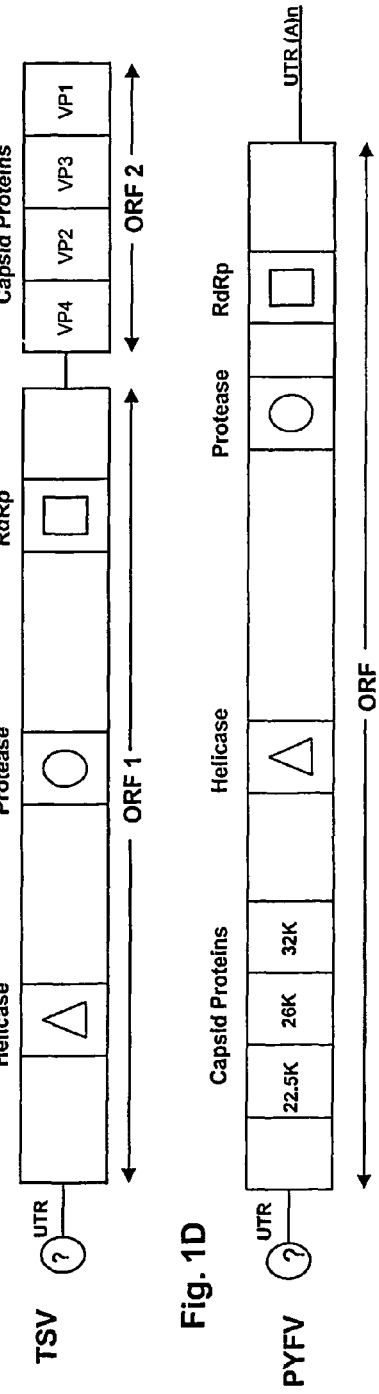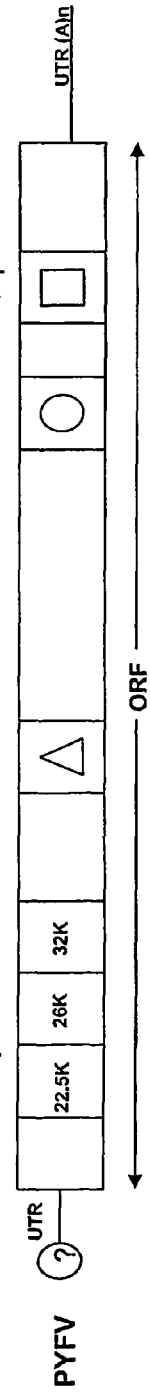

```
CrPV    1 ------------------------------AAAATGTGATCTTGC-TTGTAAATAC-------A
DCV     1 ---------------------------TTAAGATGTGATCTTGC-TTCCTTATAC-------A
PSIV    1 ------------------------------CTATGTGATCTTA--TTAAATTAGGT----TA
HiPV    1 -----------------------------------------TCTGA--TTAGAAGTAAG---A
BQCV    1 ----------------TTTCTTGACTTCTCTTAAAACCAACAATGTGATCTTGC-TTGCGGAGGCA-------A
TrV     1 -----------------------------------------TCTTGC-TTTCG--TAA----TA
RhPV  351 CATATATATGTCAACCCTGCTCATTGGTTTAAT-TGAGCGCAT-TTAGTGTTGTG----TG
TSV     1 ---------------------------TAGCACCACCCGATCGTAAACTCCATGTATTGGTTA
ABPV    1 ---------------------------TTAAGAATTGCAACACAACAACATGGT---TACCCA-TA
```

Fig. 2A

```
CrPV   27  ATTTTGAGAGGTTAATAA---AT-TACA-AGTAG-TGC---TATTT-TTGTATTTAG---GTT
DCV    29  ATTTTGAGAGGTTAATAA---GA-AGGA-AGTAG-TGC---TATCT-TAATAATTAG---GTT
PSIV   28  AATTTC-GAGGTTAAAAAT-AG-TTTT-AATAT-TGC---TATAG-TCTTAGAGGT---CTT
HiPV   18  AAATTCCTAGTT--ATAAT-AT-TTTT-AATAC-TGC---TACAT-TTTTAAGACC---CTT
BQCV   52  AATTTGCACAGT---ATAAA-ATCTGCA-AGTAG-TGC---TATTG-TTGGAATCAC---CGT
TrV    17  AAATTC---T-GTACATAAA-AGTCGAA-AGTAT-TGC---TATAG-TTAAGGTTGCG-CTT
RhPV  407  ATCTTGCGCGATAAAATGCTGACGTGAA-AACGT-TGCG-TATTG-CTACAACACTTGGTT
TSV    37  CCCATCTGC-ATCGAAAACTCTCCGAACACTAGGTGCAGTAAGGCTTTCATGGAGTGGTT
ABPV   33  AATTGAGGAAATTTCCAATAAACTCGATTTTAA-GGCT-TGTGTTGGACAAG---GTG

CrPV   77  AGCTATTTAGCTTTTACGTTCCAGGATGCCTAG-TGGCAGCCCCA-CAATATCC----AGGA
DCV    79  AACTATTTAGTTTTACTGTTCAGGATGCCTAT-TGGCAGCCCCA-TAATATCC----AGGA
PSIV   78  GTATATTTATACTTACCACACAAGATGACCG-GAGCAGCCCTC-CAATATCT----AGTG
HiPV   67  AGTTATTTAGCTTTTACCGCCCCAGGGGGTG-CAGCGTTCCTG-CAATATCC----AGGG
BQCV  102  ACCTATTTAGGTTTTACGCTCCAAGATCGGTGGATAGCAGCCCTATCAATATCT---AGGA
TrV    67  GCCTATTTAGGCATACTTCTAGGATGCCGCG-TTGCAGTCCAA-CAAGATCC----AGGG
RhPV  519  AGCTATTTAGCTTTTACTAATCAAGAGCCGTC-GTGCAGCCCAC-AAAAGTCT---AGAT
TSV    96  TGCTATTAGCG-TACGTGT-ACCATAG------GCAGCCCAAAAACACGTGTGAGGA
ABPV   89  CCCTATTTAGGGTGAGGAGCCTTACTGG----------CAGCCCCAGTGA-ATCCTATTG
```

Fig. 2B

```
                      Stem                    Loop            Stem
CrPV  132  AGCCCTCTCTGCGGTTTTCAGAT---TAG---GTAGTCGAAAAACCTAAGAAATTTACCT----
DCV   134  CACCCTCTCTGCTCTTCTTATATGAT-TAG---GTTGTCATTTAGAATAAGAAAATAACCT----
PSIV  133  TACCCTCG-TGCTCGCTCAAACAT---TAA---GTGGTGTTGTGCGAAAAGAATCTCACTT----
HiPV  122  CACC-TAGGTGCAGCCTTGTAGTT---TTA---GTGGACTTTAGGCTAAAGAATTTCACTA----
BQCV  159  GAAC-TGTGCTATGTTTTAGAAGAT--TAG---GTAGTCTCTAAACAGAACAATTTA--------
TrV   122  A-----CTGTACAGAGAGAGCATACGC-TAC---CTCGAGTC---GGGTTTGGAATCTAAGGTTGA
RhPV  167  A---CGTCACAGGAGAGAGCATACGC-TAG---GTCGCGTTG-ACTATCCTATAT----------
TSV   666  GAAAGTCCCAGTCCACTTGGGCAAAGTAGACAGCCGCTTGCGTTGGACTTAATTA----------
ABPV  140  GA---TAGGAACAGCT---ATA--T--TGG---GTAGTTGT--AGCAGTTGTATTTAA-------
```

Fig. 2C

```
WSSVT: 1221  MCELDILHDSLYQFCPELHLKRINSLTLACHALLDCKTLTLTELGRNLPTKARTKHNIKR  1042
SESET:    1  MCELDILHDSLYQFCPELHLKRINSLTLACHALLDCKTLTLTELGRNLPTKARTKHNIKR    60

WSSVT: 1041  IDRLLGNRHLHKERLAVYRWHASFICSGNTMPIVLVDWSDIREQKRLMVLRASVALHGRS   862
SESET:   61  IDRLLGNRHLHKERLAVYRWHASFICSGNTMPIVLVDWSDIREQKRLMVLRASVALHGRS   120

WSSVT:  861  VTLYEKAFPLSEQCSKKAHDQFLADLASILPSNTTPLIVSDAGFKVPWYKSVEKLGWYWL   682
SESET:  121  VTLYEKAFPLSEQCSKKAHDQFLADLASILPSNTTPLIVSDAGFKVPWYKSVEKLGWYWL   180

WSSVT:  681  SRVRGKVQYADLGAENWKPISNLHDMSSSHSKTLGYKRLTKSNPISCQILLYKSRKGRK   502
SESET:  181  SRVRGKVQYADLGAENWKPISNLHDMSSSHSKTLGYKRLTKSNPISCQILLYKSRSKGRK   240

WSSVT:  501  NQRSTRTHCHHPSPKIYSASAKEPWILATNLPVEIRTPKQLVNIYSKRMQIEETFRDLKS   322
SESET:  241  NQRSTRTHCHHPSPKIYSASAKEPWILATNLPVEIRTPKQLVNIYSKRMQIEETFRDLKS   300

WSSVT:  321  PAYGLGLRHSRTSSSEREFDIMLLIALMLQLTCWLAGVHAQKQGWDKHFQANTVRNRNVLS   142
SESET:  301  PAYGLGLRHSRTSSSEREFDIMLLIALMLQLTCWLAGVHAQKQGWDKHFQANTVRNRNVLS   360

WSSVT:  141  TVRLGMEVLRHSGYTITREDSLVAATLLTQNLFTHGYVLGKL    16
SESET:  361  TVRLGMEVLRHSGYTITREDSLVAATLLTQNLFTHGYVLGKL   402
```

Fig. 6

```
Shrimp      16  LPTNVELQLIRLCVESN-FFSFEGRFYSQTFGVAMGSPLYPVLANLFMEFFESELLPSIS  192
                +P  +F+ ++R C+E N +F +E + Y+Q  G+ MGSP  PV+A++ ME       ++      +
Fruit fly  466  IPKQLFMDIVRFCIEENRYFKYEDKIYTQLKGMPMGSPASPVIADILMEELLDKITDKLK  525

Shrimp     193  LRPSVWLRYVDDVALWPHDPALFPDFLMRLNSLSPSIREKVEWEVDNKLPFLDTLVHRSA  372
                ++P +  +YVDD+             +   +  + L LNS     I+F +E E D KLPFLD++V R
Fruit fly  526  IKPRLLTKYVDDLFAITNKIDV-ENILKELNSFHKQIKFTMELEKDGKLPFLDSIVSRMD  584

Shrimp     373  EHFSFFICRKPMHSGMYITLLSYHP  447
                       RKP+ SG   +     S HP
Fruit fly  585  NTLKIKWYRKPIASGRIINFNSNHP  609
```

Fig. 8

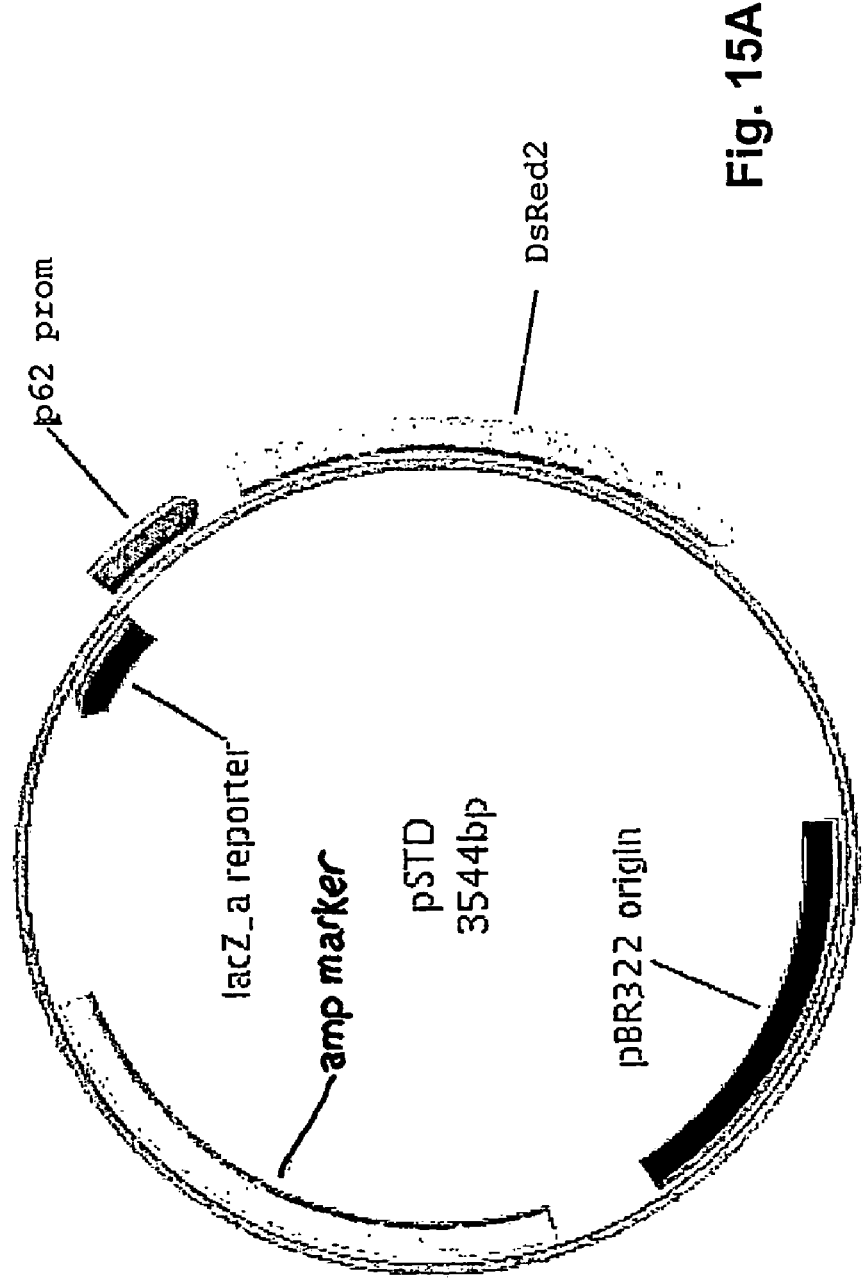

CRUSTACEAN EXPRESSION VECTOR

BACKGROUND OF THE INVENTION

Fish and shellfish farming significantly contribute to the global food supply and is a source of a major economic activity in developing nations (FAO Fisheries department, 2000). As the supply of food fish and shellfish from capture fisheries declines globally, there is an urgent need to enhance aquaculture production. The development of aquaculture in a sustainable manner faces a number of challenges. Among them diseases caused by diverse etiologic agents is of particular importance. Disease outbreaks and emergence of new pathogens poses a major challenge for sustainable development in aquaculture. A case in point is shrimp aquaculture.

During the past decade, shrimp (Penaeus sp.) farming has evolved from subsistence level farming to a major worldwide industry providing jobs to millions of people both directly and indirectly, particularly in the coastal areas of the developing nations in the Asia and the Central and South Americas. Among the challenges facing shrimp farming globally, economic losses from diseases caused by viruses are a major concern. Since the first report of a viral disease in early 1970s, more than 20 viruses have been reported that infect shrimp (Lightner, 1996, Rev. Sci. Tech. Off. Int. Epiz. 15:579-601). This list is growing rapidly. Many of shrimp viruses have caused serious epizootics in penaeid shrimp resulting in significant economic losses to commercial shrimp farmers and potentially affecting wild crustacean populations adversely. The four most important viruses of penaeid shrimp are white spot syndrome virus (WSSV), yellowhead virus (YHV), Taura syndrome virus (TSV) and the infectious hypodermal and hematopoietic necrosis virus (IHHNV). WSSV, YHV, and, more recently, TSV have caused serious epizootics in the Eastern Hemisphere; whereas, WSSV, TSV and IHHNV related economic losses have occurred in the Western Hemisphere (Dhar et al., 2004, Adv. Virus Res., In press; Tu et al., 1999, Dis. Aquat. Org. 38:159-161; Lightner et al., 1996, Rev. Sci. Tech. Off. Int. Epiz. 16:146-160). Considerable progress has been made in developing detection methods and characterizing these viral pathogens at molecular level over the last few years. However, information on the role of the virally encoded proteins in viral pathogenesis and the genes involved in host anti-viral response remains largely unknown. This is primarily because of: (1) a lack of a suitable transient and transfection vectors for shrimp and other crustaceans and (2) a lack of a permanent cell line for shrimp and any other crustaceans.

The instant invention addresses these issues by developing expression vectors for transient expression of foreign genes, and for transfection of shrimp primary cell lines with foreign genes or modifiers of endogenous genes. These vectors could be used (1) to express recombinant protein(s) with therapeutic potential using shrimp or other crustacean host, (2) to express host gene or foreign gene in excess to determine their role in growth, development, and or disease resistance using shrimp or other crustacean host, (3) to develop a transgenic shrimp or other crustaceans, and (4) to study the role of virally encoded protein in viral pathogenesis in vitro and in vivo. These techniques will develop the tools needed to modify primary cell cultures to enable the development of unregulated growth necessary for immortalized cell lines.

SUMMARY OF THE INVENTION

The inventors have discovered a number of important tools that will enable the manipulation of animal genes both transiently and permanently in both tissue culture and live animals. In general, the invention harnesses elements from shrimp viruses that through bioinformatics evaluation have been shown to have homology to enhancer or regulatory elements in other species. The inventors have demonstrated specific vectors that can be developed from these elements and methods of their use in the instant invention that will allow the improvement of animal health as well as diagnostic uses thereof. Specifically the invention relates to improvement of crustacean and especially shrimp health in relation to virally transmitted disease. The invention also provides tools for drug development and diagnostics of the same.

It is an object of the invention to provide a transient expression vector for the expression of a foreign gene or genes in Penaeid shrimp tissues in vitro or in vivo.

It is a further object of the invention to provide a transient expression vector for the expression of a foreign gene or genes in bacteria and yeast.

It is an object of the invention to provide a transfection vector for the expression of a foreign gene or genes in Penaeid shrimp tissue in vitro or in vivo.

It is an object of the invention to provide a transfection vector for developing transgenic shrimp expressing a foreign gene or shrimp gene or any combination thereof.

It is an object of the invention to provide a transient and a transfection vector for developing a permanent cell line for shrimp, crustaceans, and mollusks by over expressing host telomerase gene or introduction of a heterologous telomerase gene.

It is an object of the invention to provide a transfection vector for developing transgenic fish, shellfish or insects expressing a foreign gene or genes. Such a vector would have a broad host range that may be applicable to other animals as an expression system.

It is an object of the invention to provide methods of transient expression in crustaceans, fish, shellfish, insects, or other cell culture based on the vectors developed herein.

It is an object of the invention to provide methods for transfection in crustaceans, fish, shellfish, insects, or other cell culture based on the vectors developed herein.

It is an object of the invention to provide methods of protecting shrimp from WSSV, IHHNV, TSV, YHV and other viral, bacterial and fungal diseases by over expressing antiviral/antimicrobial factors using the transfection vector.

It is an object of the invention to provide methods of protecting shrimp from WSSV, IHHNV, TSV, YHV and other viral, bacteria, and fungal diseases by over expressing pathogen-encoded protein (e.g., capsid protein) using the transfection vector.

It is an object of the invention to provide methods of protecting fish and shellfish from viral, bacterial, fungal and or other microbial infection by over-expressing antiviral/antimicrobial factors using the transfection vector for delivery of the therapeutic effect.

It is an object of the invention to provide methods of protecting fish and shellfish from viral, bacterial, fungal and or other microbial infection by over expressing pathogen-encoded protein or proteins (e.g., capsid protein, enzyme, receptor, recognition sequence) using the transfection vector.

Therefore, the invention provides a composition for developing a transient or transfection vector using sequences of shrimp virus and shrimp cellular gene as well as the methods for using such vectors for manipulation of cells and diagnostic applications. Such vectors could be used for the expression of recombinant protein in vitro or in vivo in shrimp or other crustaceans, fish, insects, and other animals.

BRIEF DESCRIPTIONS OF THE FIGURES

FIG. 1 consists of FIGS. 1A, 1B, 1C, and 1D. A comparative representation of the genomic organization of several mammalian and insect picomaviruses and plant RNA viruses—PV in FIG. 1A, IFV in FIG. 1B, TSV in FIG. 1C, and PYFV in FIG. 1D. Abbreviations used are as follows: ORF=Open reading frame; UTR=untranslated region; VPg=genome linked protein; and ?=the presence of VPg has not been confirmed. The helicase (triangle), protease (circle), and the RNA dependent RNA polymerase (square) regions are indicated.

FIG. 2 consists of FIGS. 2A, 2B, and 2C. In these figures, the intergenic regions between ORF1 and ORF 2 of TSV are aligned and compared with the homologous regions of insect picoma-like viruses. The sequences in FIG. 2A continue in FIG. 2B, and those in FIG. 2B continue in FIG. 2C. Nucleotide residues indicated in bold, underlined text are conserved residues, underlined (but not bold) residues are partially conserved among the sequences, and residues indicated in ordinary text appear not to be conserved. The numbers presents the corresponding number of the first nucleotide in the intergenic region between ORF1 and ORF2, except that in order to improve the alignment, the first 350 nucleotide residues of RhPV are not shown. Corresponding SEQ ID NOs: are, for cricket paralysis viruse (CrPV), SEQ ID NO: 1; for Drosophila C virus (DCV), SEQ ID NO: 2; for Plautia stali intestine virus (PSIV), SEQ ID NO: 3; for Himetobi P virus (HiPV), SEQ ID NO: 4; for black queen cell virus (BQCV), SEQ ID NO: 5; for triatoma virus (TrV), SEQ ID NO: 6; for Rhopalosiphum padi virus (RbPV), SEQ ID NO: 7; for Taura syndrome virus (TSV), SEQ ID NO: 8; for acute bee paralysis virus (ABPV), SEQ ID NO: 9.

FIG. 3 is a schematic representation of the genome organization of IHHNV, based on the sequence of GenBank accession no. AF273215. The numbers on the diagram indicate nucleotide residue numbers. The left open reading frame (ORF) starts at nucleotide residue 313 and ends at residue 2596, the middle ORF starts at nucleotide residue 534 and ends at residue 1631, and the right ORF starts at nucleotide residue 2535 and ends at residue 3527. The IHHNV promoters, P2 and P61, are indicated by open triangles.

FIG. 4 is an image of results of an agarose gel electrophoreses of the IHHNV P61 amplicon. PCR amplified DNA was electrophoresed in a 1.5% agarose gel containing ethidium bromide and imaged. An arrow indicates the 165 residue P61 amplicon. M represents a 100 base pair DNA ladder standard. Lanes 1 through 4 represent DNA from 4 different IHHNV-infected shrimp that was used for PCR.

FIG. 5 is a circular nucleotide map of the WSSV DNA genome (Thai-isolate, GenBank accession no. AF369029). The nucleotide residue designated 1 is the nucleotide A of ATG codon of the capsid protein gene VP28. The arrangement of all putative genes in both strands is shown by boxes on the ring inside the scale. Bars on the dashed line indicate the location of the repeat regions throughout the genome. The locations of the viral capsid genes (VP) are indicated by bars on the dotted line in the map. The ring within the ring indicating viral capsid genes indicates the GC skew, and the ring in the center represents G skew.

FIG. 6 is a BLASTX search and amino acid alignment of WSSV transposase amino acid sequence (SEQ ID NO: 10; WSSVT is the transposase of WSSV-Taiwan isolate ORF 166) and a bacterial transposon amino acid sequence (SEQ ID NO: 11; SESET is a transposon of Salmonella enterica subsp. enterica serovar Typhi; GenBank Accession no. 16760800).

FIG. 7 is a schematic map of the transposase gene in WSSV isolate Taiwan (GenBank accession number AF440570). Inverted repeat sequences are indicated by the abbreviation IR. Viral repeat sequence (SEQ ID NO: 12) is indicated in the Repeat box. The numbers on top of the boxes (238587 and 239925) indicate the nucleotide position in the genome of the WSSV-Taiwan isolate. The length 1337 bp indicates the length of transposase gene, in base pairs. The palindromic sequence within the inverted repeat sequences (SEQ ID NOs: 13 and 14) is underlined.

FIG. 8 is a BLASTX search and amino acid sequence alignment of shrimp DNA clone AF077579 amino acid sequence (SEQ ID NO: 15; "Shrimp"; Xu et al., 1999, Animal Genet. 30:1-7) and the non-LTR Penelope transposable element of Drosophila virilis amino acid sequence (SEQ ID NO: 16; from GenBank Accession no. Q24736).

FIG. 9, consisting of FIGS. 9A and 9B, is a schematic representation of shrimp expression vectors described herein. The vector diagramed in FIG. 9A is a transient expression vector containing the IHHNV P61 promoter, IRES element of the TSV intergenic region between ORF1 and ORF2, and a marker gene. The vector diagramed in FIG. 9B is a transfection vector for shrimp containing the IHHNV P61 promoter, shrimp Penelope full-length ORF, TSV IRES element and a selectable marker (e.g., pDsRed). Shrimp Penelope represents the full-length copy of the Penelope gene from shrimp. Arrows marked by 5' and 3' represent the positions of the shrimp Penelope element inverted terminal repeats.

FIG. 10 is a schematic representation of a shrimp transfection expression vector described herein. A transfection vector for shrimp can contain the IHHNV P61 promoter, full-length WSSV transposase gene, TSV IRES element and a selectable marker (e.g., pDsRed). Arrows marked by 5' and 3' represent the positions of the WSSV inverted terminal repeats.

Figure 15B:
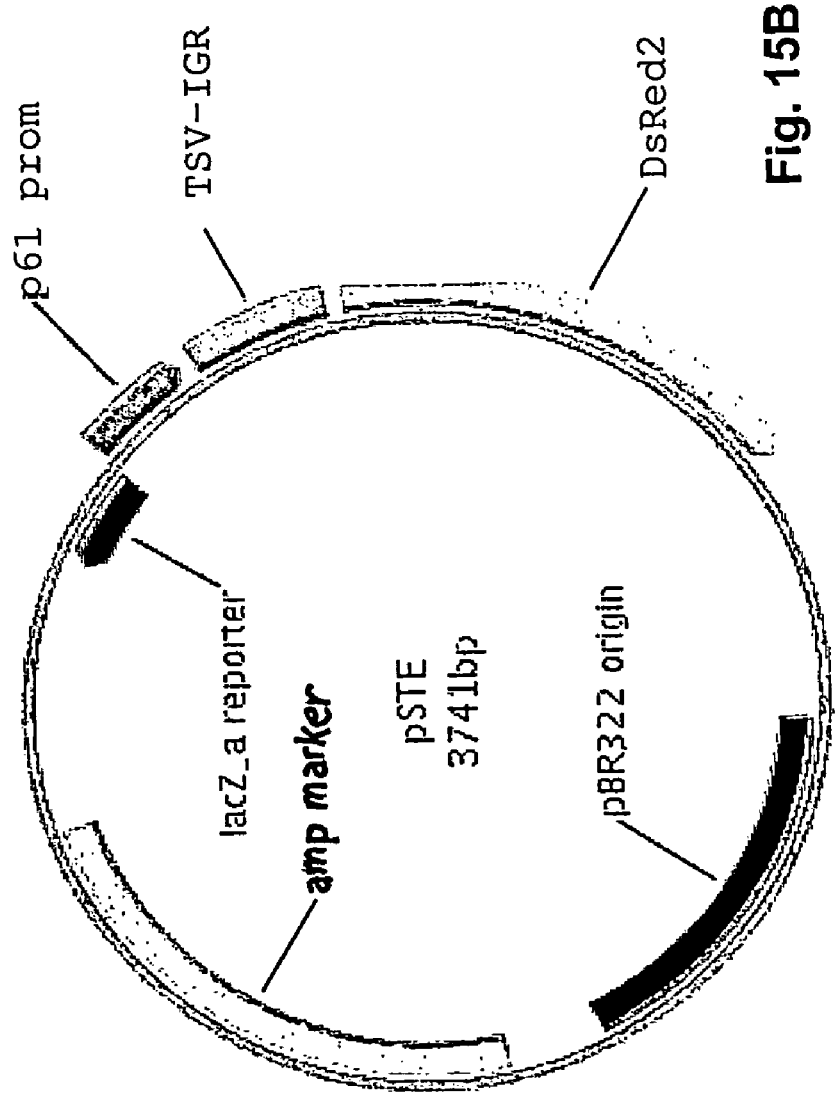

FIG. 15, consisting of FIGS. 15A and 15B, is a pair of plasmid maps of IHHNV p61 promoter driving DsRed2 expression without added IRES element (PSTD, shown in FIG. 15A) and with the TSV IRES element (PSTE, shown in FIG. 15B).

Figure 16:
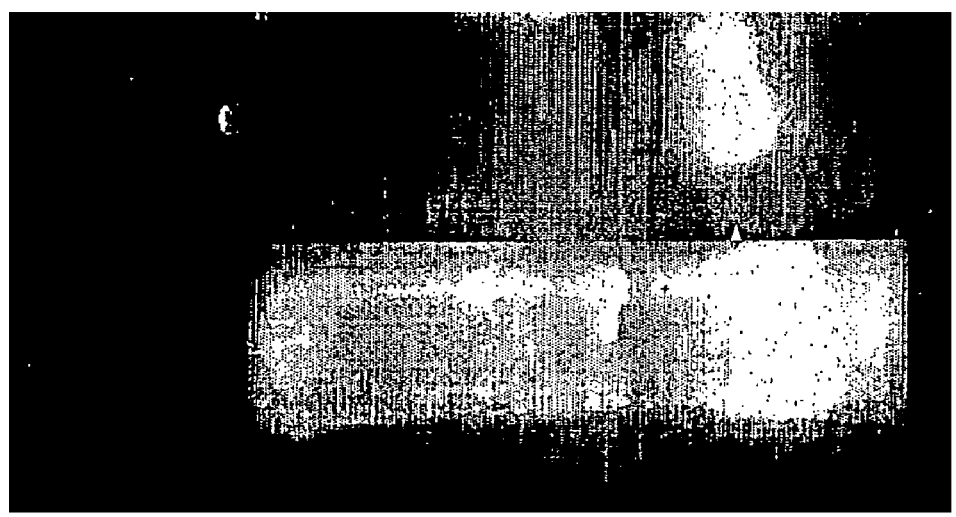

FIG. 16 is an image of an agarose gel separation of the digest described in Example 16 herein. Lane 1 contains a 100 base pair DNA ladder standard. Lane 2-TSV contains the IRES PCR product.

Figure 17:
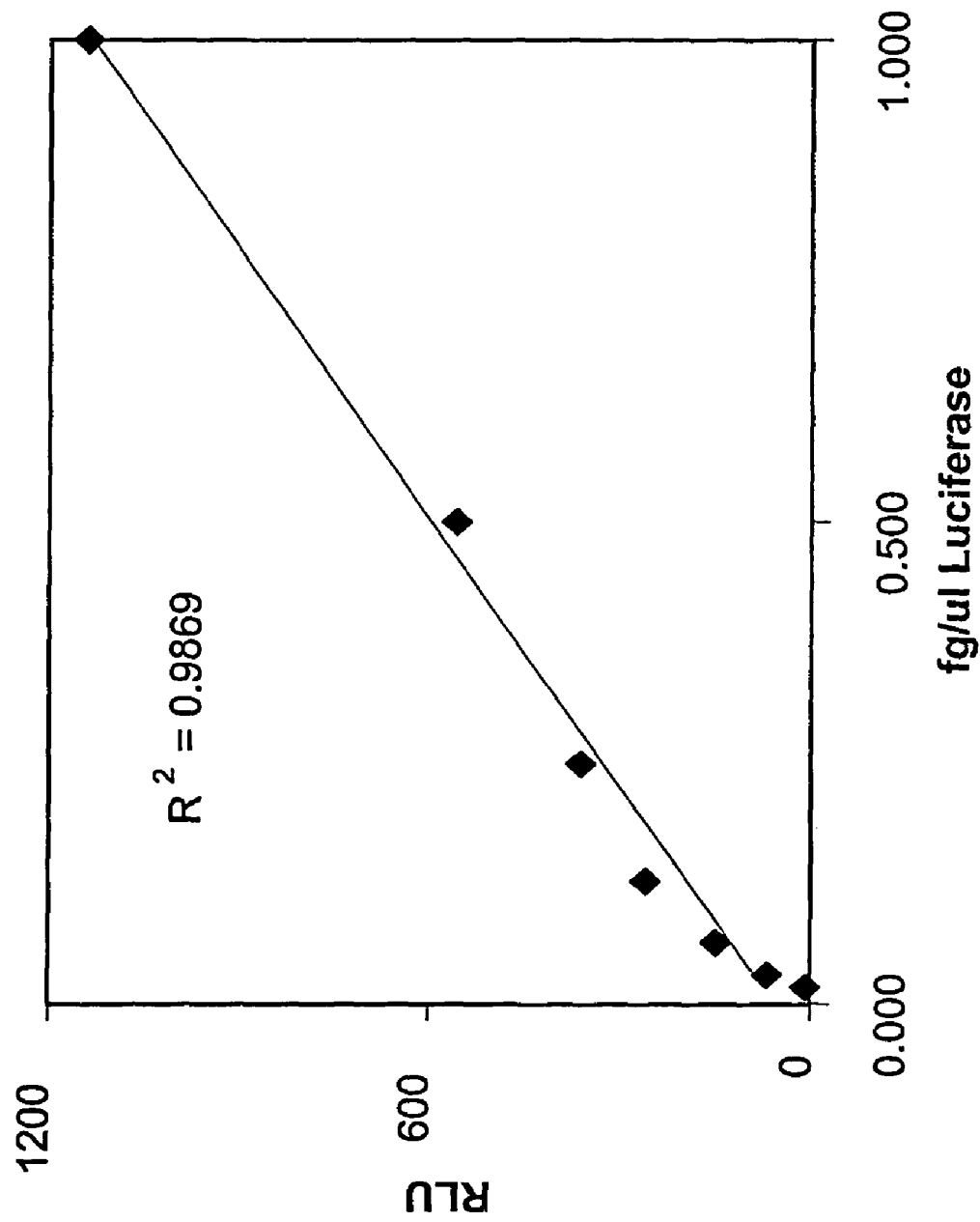

FIG. 17 is a standard curve generated for the luciferase assay used to determine expression of luciferase in shrimp tissues, as described in Example 17 herein.

DETAILED DESCRIPTION OF THE INVENTION

The invention relates to compositions and methods that can be used to express heterologous nucleic acids and proteins in cells of marine creatures, including crustaceans such as shrimp, lobster, crayfish, and crabs, and further including non-crustacean arthropods and other marine animals such as fish and mollusks.

The invention relates to a non-naturally-occurring nucleic acid construct that includes at least a viral promoter region and an insect picornavirus (IPV) internal ribosome entry site (IRES). One or both of the promoter and the IRES can be linked with one or more cistrons, such as an intron-free open reading frame (ORF). Significantly, it has been discovered that use of a virus promoter and an IRES from an IPV renders the construct capable of expressing in a crustacean cell RNA or protein encoded by a nucleic acid introduced into the cell as part of the construct. Such constructs can be used to produce one or more nucleic acids in a host crustacean cell. By way of example, an mRNA encoding a protein of interest can be produced, as can an RNA that binds with a specific endogenously-produced nucleic acid of the cell. Further by way of example, a protein encoded by a portion of the construct can produced in a crustacean cell by incorporating into the cell a construct in which the portion is operably linked to a viral promoter to generate RNA that includes both the portion and an IPV IRES, which can be translated by the host cell to produce the protein.

The identities of the virus from which the promoter and the IPV from which the IRES are derived is not critical. Preferably, the promoter and the IRES are derived from the same IPV, but elements from distinct viruses can be used as well. The IPV(s) can be substantially any IPV that is currently known or hereafter developed. A preferred type of IPV is the class of IPVs that are designated "cricket paralysis-like" picornaviruses, as described in the art (e.g., Christian et al., 1998, In: Miller et al., Eds., "The Insect Viruses" New York, Plenum Press, pp. 301-329; van Regenmortel et al., 2000, In: "Virus Taxonomy: The Classification and Nomenclature of Viruses. The Seventh Report of the International Committee on Taxonomy of Viruses" Academic Press, San Diego). It is recognized that it is not always possible to distinguish picornaviruses from other RNA-containing viruses which exhibit significant morphological, physical, and chemical similarity to picornaviruses. Thus, the art recognizes a group of "picorna-like" viruses, such as TSV of shrimp. As used herein, the term IPV includes both viruses that are capable of infecting hosts in phylum Arthropoda, regardless of whether they are designated "picornaviruses" or "picorna-like viruses."

Knowledge of the identity of a host cell into which a nucleic acid construct of the type described herein will be incorporated can guide selection of an appropriate IPV. It has been discovered that promoters from substantially any virus (at least viruses suitable for any actual or anticipated host for the construct) and IRES' from substantially any IPV can be used in vectors intended for use in crustaceans. Nonetheless, it can be preferable to select a promoter, an IRES, or both, from a virus that is known to infect crustaceans of the same species as the crustacean from which the host cell was derived. Thus, for example, if a nucleic acid construct described herein is to be used to produce a protein upon incorporation into shrimp cells, it can be preferable to use a promoter and IRES from among those of known shrimp viruses, such as infectious hypodermal and hematopoietic necrosis virus (IHHNv), Taura syndrome virus (TSV), or white spot syndrome virus (WSSV).

The properties of many viral promoters are known, including multiple IPV promoters. Substantially any viral promoter can be used in the nucleic acid constructs described herein.

Examples of suitable promoters include promoters from TSV, IHHNV, and WSSV (e.g., the P2 or P61 promoter of WSSV).

In many picornaviruses, especially including those having genes arranged in a single polycistronic unit, an IRES occurs in the 5'-untranslated region of the viral genome. In other picornaviruses, an IRES occurs in the intergenic region between two or more cistronic regions of the viral genome. Either type of IRES can be incorporated into the nucleic acid construct described herein.

The nucleic acid constructs described herein can be designed to express a product for a relatively short time or for a longer period, such as the lifetime of a host cell or organism, or even across generations of organisms. The association between the form of a nucleic acid construct (e.g., straight-chain nucleic acid, plasmid, or viral vector) and its duration in vivo are known and a skilled artisan can influence the duration of product production from the construct by selection of a suitable form of the construct.

Duration of product production can also be influenced by the properties of the genetic elements included in the construct. By way of example, the promoter that is used can be an inducible or repressible promoter, subject to regulation by its effectors. Similarly, it is known that promoters can induce transcription of an operably linked sequence at a high or low level, depending on the identity of the promoter and the host organism.

Residence in a host cell of a construct described herein can be influenced by the presence or absence of genetic elements in the construct. By way of example, if the construct in introduced into a host cell in the form of a plasmid, the plasmid (together with the construct) will be replicated if the plasmid includes an origin of replication site (ORS) that is operable in the host cell. It is known that ORS can induce maintenance of single, a few, or multiple copies of a plasmid in a cell, and a skilled artisan can select an appropriate ORS for a desired copy number for a desired host cell. Further by way of example, if the construct is included in a virus vector construct that is capable of replication and packaging (or can be induced to replicate and package), then maintenance or spread of the construct can be controlled using methods understood by a skilled artisan in this field.

One or more cistronic elements (e.g., an ORF) can be operably linked with the IRES of the construct, to thereby allow expression of the protein or protein subunit encoded by the cistron. The cistronic element should also be operably linked with the promoter, so as to enhance transcription of RNA encoding the cistron prior to translation brought about by introduction of a ribosome into the RNA by way of the IRES (or by a normal, mRNA cap-targeted ribosome or both). The cistron is preferably an ORF that is not interrupted by an intron, but one or more introns can be present so long as the host cell is able to remove the intron(s) to yield the construct-encoded product of interest.

A cistron of the construct can encode an RNA that has a physiological effect on the host cell (e.g., one that hybridizes specifically with a nucleic acid in the cell). The cistron can also encode a protein. For example, if the cell is a cell of a crustacean food product (e.g., a farm-raised shrimp), the protein can be one which enhances the human nutritional value, the health of the crustacean, or the disease resistance of the crustacean. Proteins which enhance the lifespan, physiology or rate of proliferation of an individual cell are further examples of proteins that can be expressed in a host cell from the nucleic acid construct described herein.

It is known that a protein or nucleic acid expressed in a cell can exert a direct physiological effect on a cell (e.g., a protein that catalyzes a chemical reaction or is a structural component of a cell or a nucleic acid that binds with a cellular nucleic acid in way that affects expression of the cellular nucleic acid). It is also known that a protein or nucleic acid expressed in a cell can exert a relatively indirect physiological effect on a cell (e.g., a protein that acts as a transcription factor or a nucleic acid that modulates the activity of a cellular nucleic acid polymerase). It is immaterial which of these (or other) types of products is produced from a nucleic acid construct described herein when the construct is introduced into a host cell. A skilled artisan can select an appropriate product based on the identity and biochemical properties of the host cell and the desired effect, and no more than ordinary experimentation is required to make a construct that produces the appropriate product. Such products can be products that are ordinarily produced in the host cell (e.g., at a different level in the presence and absence of the construct) or can be heterologous products (e.g., products unlike any produced by the host cell or an altered form of a homologous product).

A transposable element (TE) can be included in the construct if desired. A TE facilitates distribution of operably linked elements of the construct into the genome of the host cell. A TE can thereby incorporate a transgene from the construct described herein (transiently or relatively permanently, depending on the TE selected) into the host genome. A skilled artisan is able to operably link selected elements of the construct described herein with a TE with no more than routine experimentation. Examples of suitable TEs include those that are homologous to the *Drosophila Penelope* TE sequence reported in the literature. Other suitable TEs include IPV TEs, such as those of WSSV.

In an important embodiment, the nucleic acid construct described herein can be used to express a protein in a host cell, such as a crustacean cell. This is achieved by introducing into the host cell one or more copies of the nucleic acid construct described herein. The method by which the construct is introduced into the host cell is not critical, and a variety of methods of introducing a nucleic acid vector into a cell are known in the art. Examples of suitable methods of incorporating the construct into a host cell include use of a virus vector containing the construct, a ballistically administered particle coated with or containing the construct, and electroporesis of cells in the presence of a plasmid that includes the construct.

Definitions

In describing the present invention, the following terminology is used in accordance with the definitions set out below.

"Shrimp" refers to any of the group of crustaceans that are commonly cultured for aquaculture or captured in the wild fisheries. The term "shrimp" includes shrimp eggs, shrimp larvae, shrimp post-larvae and adult shrimp. The term "shrimp" and "prawn" will be used interchangeably throughout the specification. Shrimp can refer to but are not limited to, *Penaeus* shrimp and include the species *Penaeus vannamei, Penaeus chinensis, Penaeus monodon, Penaeus stylirostris, Penaeus japonicus, Penaeus penicillatus, Penaeus merguiensis, Penaeus indicus, Penaeus subtilis, Penaeus paulensis, Penaeus setiferus, Penaeus brasiliensis, Penaeus duorarum, Penaeus occidentalis, Penaeus schmitti, Penaeus californiensis, Penaeus semisulcatus, Penaeus latisulcatus, Metapenaeus monoceros, Metapenaeus dobsoni, Metapenaeus affinis, and Metapenaeus brivicornis*; and *Litopenaeid* shrimp (such as *Litopenaeus vannamei, L. setiferus*).

A "vector" comprises a nucleic acid, which can infect, transfect, and transiently or permanently transform or transfect a cell. It will be recognized that a vector can be a naked nucleic acid, or a nucleic acid complexed with protein or lipid. The vector optionally comprises viral or bacterial nucleic acids and/or proteins, and/or membranes (e.g., a cell membrane, a viral lipid envelope, etc.). Vectors include, but are not limited to replicons (e.g., RNA replicons, bacteriophages) to which fragments of DNA may be attached and become replicated. Vectors thus include, but are not limited to RNA, autonomous self-replicating circular or linear DNA or RNA (e.g., plasmids, viruses, and the like, see, e.g., U.S. Pat. No. 5,217,879), and include both the expression and non-expression plasmids. Where a recombinant microorganism or cell culture is described as hosting an "expression vector" this includes both extra-chromosomal circular and linear DNA and DNA that has been incorporated into the host chromosome(s). Where a vector is being maintained in a host cell, the vector may either be stably replicated by the cells during mitosis as an autonomous structure, or is incorporated within the host's genome.

The term "promoter" includes all sequences capable of driving transcription of a coding sequence in a cell, e.g., a plant cell, animal cell, bacterial cell, fungal cell, and yeast cell. Thus, promoters used in the constructs of the invention include cis-acting transcriptional control elements and regulatory sequences that are involved in regulating or modulating the timing and/or rate of transcription of a gene or genes. For example, a promoter can be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. These cis-acting sequences typically interact with proteins or other biomolecules to carry out (turn on/off, regulate, modulate, etc.) transcription. "Constitutive" promoters are those that drive expression continuously under most environmental conditions and states of development or cell differentiation. "Inducible" or "regulatable" promoters direct expression of the nucleic acid of the invention under the influence of environmental conditions or developmental conditions. Examples of environmental conditions that may affect transcription by inducible promoters include anaerobic conditions, elevated temperature, drought, or the presence of light.

"Plasmids" can be commercially available, publicly available on an unrestricted basis, or can be constructed from available plasmids in accord with published procedures. Equivalent plasmids to those described herein are known in the art and will be apparent to the ordinarily skilled artisan.

"Transposable elements" (TEs) or "transposons" are a group of genetic elements that move from one locus to another by non-homologous recombination.

"Internal ribosome entry site" or "IRES" refers to a translation control element for cap independent mRNA translation. IRES' have been described in the art (e.g., see review by Hellen et al., 2001, Genes Develop. 15:1596-1612), and a skilled artisan is able to operably link an open reading frame or cistron with an IRES with no more than routine experimentation.

The term "gene" includes a nucleic acid sequence comprising a segment of DNA involved in producing a transcription product (e.g., a message), which in turn is translated to produce a polypeptide chain, or regulates gene transcription, reproduction or stability. Genes can include regions preceding and following the coding region, such as leader and trailer, promoters and enhancers, as well as, where applicable, intervening sequences (introns) between individual coding segments (exons).

The phrases "nucleic acid" or "nucleic acid sequence" includes oligonucleotide, nucleotide, polynucleotide, or to a fragment of any of these, to DNA or RNA (e.g., mRNA, rRNA, tRNA) of genomic or synthetic origin which may be single-stranded (ss) or double-stranded (ds) and may represent a sense (+) or antisense (−) strand, to peptide nucleic acid (PNA), or to any DNA-like or RNA-like material, natural or synthetic in origin, including, e.g., iRNA, ribonucleoproteins (e.g., iRNPs). The term encompasses nucleic acids, i.e., oligonucleotides, containing known analogues of natural nucleotides. The term also encompasses nucleic-acid-like structures with synthetic backbones (see e.g., Mata, 1997, Toxicol. Appl. Pharmacol. 144:189-197; Strauss-Soukup, 1997, Biochemistry 36:8692-8698; Samstag, 1996, Antisense Nucl. Acid Drug Dev. 6:153-156).

"Amino acid" or "amino acid sequence" includes an oligopeptide, peptide, polypeptide, or protein sequence, or to a fragment, portion, or subunit of any of these, and to naturally occurring or synthetic molecules. The terms "polypeptide" and "protein" include amino acids joined to each other by peptide bonds or modified peptide bonds, i.e., peptide isosteres, and may contain modified amino acids other than the 20 gene-encoded amino acids. The term "polypeptide" also includes peptides and polypeptide fragments, motifs and the like. The term also includes glycosylated polypeptides. The peptides and polypeptides of the invention also include all "mimetic" and "peptidomimetic" forms, as described in further detail, below.

The term "isolated" includes a material removed from its original environment, e.g., the natural environment if it is naturally occurring. For example, a naturally occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment. As used herein, an isolated material or composition can also be a "purified" composition, i.e., it does not require absolute purity; rather, it is intended as a relative definition. Individual nucleic acids obtained from a library can be conventionally purified to electrophoretic homogeneity. In alternative aspects, the invention provides nucleic acids, which have been purified, from genomic DNA or from other sequences in a library or other environment by at least one, two, three, four, five, or more orders of magnitude.

As used herein, the term "recombinant" can include nucleic acids adjacent to a "backbone" nucleic acid to which it is not adjacent in its natural environment. In one aspect, nucleic acids represent 5% or more of the number of nucleic acid inserts in a population of nucleic acid "backbone molecules." "Backbone molecules" according to the invention include nucleic acids such as expression vectors, self-replicating nucleic acids, viruses, integrating nucleic acids, and other vectors or nucleic acids used to maintain or manipulate a nucleic acid insert of interest. In one aspect, the (isolated, recombinant, enriched) nucleic acids represent 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 92%, 94%, 95%, 96%, 97%, 98%, 99%, or more of the number of nucleic acid inserts in the population of recombinant backbone molecules. "Recombinant" polypeptides or proteins refer to polypeptides or proteins produced by recombinant DNA techniques; e.g., produced from cells transformed by an exogenous DNA construct encoding the desired polypeptide or protein. "Synthetic" polypeptides or protein are those prepared by chemical synthesis, as described in further detail, below.

A promoter sequence can be "operably linked to" a coding sequence when RNA polymerase which initiates transcription at the promoter will transcribe the coding sequence into MRNA, as discussed further, below.

"Primer" includes either a single stranded polydeoxynucleotide or two complementary polydeoxynucleotide strands, which may be chemically synthesized. Such synthetic oligonucleotides have no 5' phosphate and thus will not ligate to another oligonucleotide without adding a phosphate with an ATP in the presence of a kinase. A synthetic oligonucleotide can ligate to a fragment that has not been dephosphorylated.

All other terms are defined in the literature using Sambrook (Sambrook et al., 1989, "Molecular Cloning: A laboratory manual" Ed. 2, Cold Spring Harbor Press, Cold Spring Harbor) as a guide.

Genome Organization of the TSV

The TSV genome is a single-stranded RNA of positive polarity with a 3'-poly(A) tail (Bonami et al., 1997, J. Gen. Virol. 78:313-319). The genome is 10205 nucleotides (nt) long with a 5' untranslated region of 377 nt and a 3' untranslated region of 226 nt (Mari et al. 2002). There are two open reading frames (ORFs) in the TSV genome. ORF1 is 6324 nt long, and encodes a 2107 amino acid (aa) polyprotein with a molecular mass of 234 kDa. ORF2 is 3036 nt long and encodes a 1011 aa polypeptide with a molecular mass of 112 kDa (Mari et al., 2002, J. Gen. Virol. 83:915-926; Robles-Sikisaka et al., 2001, Arch. Virol. 146:941-952). There is an intergenic region of 226 nt between the two ORFs. ORF1 encodes non-structural proteins (helicase, a protease and a RNA-dependent RNA polymerase, RdRp), and ORF2 encodes the virion structural proteins (FIG. 1). TSV virions contain three major polypeptides, designated as VP1, VP2, and VP3 (55, 40, and 24 kDa), and one minor polypeptide (58 kDa), designated as VPO (Bonami et al., 1997, J. Gen. Virol. 78:313-319). The N-termini of VP1 to VP3 have been sequenced, and the order of these proteins in ORF2 was found to be VP2, VP1 and VP3 (Mari et al., 2002, J. Gen. Virol. 83:915-926). The N-terminal sequence of VPO has not been determined, but it has been hypothesized that it might be processed from ORF2 in a manner similar to PSIV, an insect picorna-like virus infecting the brown-winged green bug, *Plautia stali* (Sasaki et al., 1998, Virology 244:50-58). The VP2/VP1 cleavage site in TSV is conserved in insect picornaviruses: TSV (GF↓SKD), *Plautia stali* intestine virus, PSIV (GF↓SKP), *Drosophila* C virus, DCV (GF↓SKP) and *Rhophalosiphum padi* virus, RHPV (GW↓SKP) (Robles-Sikisaka et al., 2001, Arch. Virol. 146:941-952). The presumed VP1 and VP3 cleavage site in TSV (H↓A) is partially conserved with those used by insect picornaviruses Q↓(A,S, V) (Robles-Sikisaka et al., 2001, Arch. Virol. 146:941-952).

Comparison of TSV Genome Organization with Insect and Mammalian Picornaviruses.

Picornaviruses have been isolated from a wide range of insect species. Based on their biological, biophysical properties, and genome organization data these viruses were classified as a member of a newly designated group, "Cricket paralysis-like viruses" in Picornaviridae with CrPV as the type species of this group (Christian et al., 1998, In: Miller et al., Eds., "The Insect Viruses" New York, Plenum Press, pp. 301-329; van Regenmortel et al., 2000, In: "Virus Taxonomy: The Classification and Nomenclature of Viruses. The Seventh Report of the International Committee on Taxonomy of Viruses" Academic Press, San Diego). Genomes of a number of these viruses have now been sequenced. These include CrPV (GenBank accession number AF218039), DCV (AF014388), acute bee paralysis virus (ABPV, NC002548);

black queen cell virus (BQCV, AF183905) and SBV (AF092924) of honeybees; RhPV (AF022937), PSIV (AB006531), TrV (AF178440), HiPV (AB017037); IFV (AB000906) and TSV of shrimp (AF277675). Among these viruses, the genome organizations of IFV and SBV were found to be similar to that of mammalian picornaviruses. They contain a single long ORF with the capsid proteins located at the N-terminal end and the non-structural proteins at the C terminal end. In contrast, the genomes of CrPV, DCV, RhPV, PSIV, HiPV, TrV, and TSV contain two long ORFs (ORF1 and ORF2) separated by an intergenic region. For all but RhPV, the length of the intergenic region varies from 171-207 nucleotides. The intergenic region of RhPV is 525 nucleotides long. The 5' end of ORF1 contains the non-structural proteins and the 3' end of ORF2 contains the capsid proteins (FIG. 1). All of these viruses show greater sequence similarity to each other than with any of the mammalian picornaviruses.

EXAMPLES

The invention, as contemplated herein, is a composition comprising nucleotide sequence of an insect picornavirus (IPV) such as the Taura syndrome virus (TSV), infectious hypodermal and hematopoietic necrosis virus (IHHNV), or white spot syndrome virus (WSSV), and one or more cistronic elements (e.g., a shrimp gene sequence) operably linked therewith. Alternatively, the invention provides methods of protection of animals, in particular crustaceans from disease and manipulation of animals, specifically crustaceans, in vitro and in vivo. The invention provides tools critical for the production of an immortalized shrimp cell line. The following examples describe some aspects of the invention and are used for exemplification purposes only and are not intended to limit the scope of the invention in any way.

Example 1

Identification of Internal Ribosomal Entry Site (IRES) Elements in TSV and Insect Picorna-Like Viruses.

Insect picornaviruses with dicistronic genomes have two unique features. First, no sub-genomic RNA is produced for translation of the capsid proteins. Second, the coat protein cistron appears to lack an initiating methionine suggesting that the coat protein is translated through internal initiation mediated by an internal ribosomal entry site (IRES).

Functional IRES elements have been identified in the intergenic region of CrPV and PSIV (Wilson et al., 2000, Mol. Cell. Biol. 20:4990-4999; Sasaki et al., 1999, J. Virol. 73:1219-1226), and homologous sequences have been identified in TSV (Mari et al., 2002, J. Gen. Virol. 83:915-926, FIG. 2). Cap-independent translation in PSIV ORF2 has been demonstrated in vitro using a rabbit reticulocyte lysate (Sasaki et al., 2000, Proc. Natl. Acad. Sci. USA 97:1512-1515). In CrPV, the initiation codon for IRES mediated translation was identified as CCU, whereas, in PSIV and RhPV the initiation codon was found to be CUU. It has been shown that the CCU/CUU triplets are part of the inverted repeat sequence of the IRES elements which form RNA pseudoknot structures essential for IRES activity (Wilson et al., 2000, Mol. Cell. Biol. 20:4990-4999; Sasaki et al., 1999, J. Virol. 73:1219-1226). In TSV, although there is an in-frame methionine in ORF2, N-terminal sequencing of the VP2 capsid protein identified an alanine at the terminal position in the sequenced protein (ANPVEIDNFDTT, SEQ ID NO: 17; Mari et al. 2002, Refugio et al., 2001). The alanine codon is preceded by both a proline (CCU) and a methionine (AUG) codon (MP ANPVE, SEQ ID NO: 18). For methionine to be the initiation codon for TSV ORF2, MP residues would need to be removed from the mature protein. Such post-translational processing has never been found in eukaryotes and it is likely that TSV employs an IRES-mediated cap-independent mechanism for translation of the structural proteins similarly to the insect picornaviruses.

Multiple alignments of the intergenic regions of insect picorna-like viruses are shown in FIG. 2. The nucleotide difference in the intergenic region among insect picorna-like viruses was calculated using the computer program MEGA (Kumar et al., 2001, Molecular Evolutionary Genetic Analysis (MEGA) software, version 2.0, Institute of Molecular Evolutionary Genetics, Arizona State University, Ariz., USA) (Table 1). The program calculates the p-distance (nucleotide), which is defined as the proportion (p) of nucleotide sites at which the two sequences compared are different. It is obtained by dividing the number of nucleotide differences by the total number of nucleotides compared.

The nucleotide residues that constitute the stem loop structure right before the ORF2 is indicated in FIG. 2C. This region in TSV can form secondary structures like other insect picorna-like viruses, and initiate IRES-mediated cap-independent translation of TSV ORF2 that encodes capsid proteins.

In insect picorna-like viruses like DCV, it has been shown that structural proteins are produced in vast excess over non-structural proteins in virus-infected cells (Moore et al., 1980, J. Virol. 33:1-9; Moore et al., 1981, Arch. Virol. 68:1-8). This is in contrast to human picomavirus-infected cells, wherein approximately equimolar amounts of structural and non-structural proteins are produced (Ruckert, 1996, In Fields et al., Eds., "Field Virology" Lippincott-Raven, Philadelphia, Pa., pp. 609-654). The IRES-mediated translation of the coat proteins in insect picorna-like viruses with dicistronic genome, therefore, provides a mechanistic explanation for the abundance of structural compared to non-structural proteins in insect picorna-like virus infected cells. Insect picorna-like viruses with dicistronic genomes encode two distinct polyproteins: non-structural proteins encoded by the upstream ORF and the structural protein encoded by the downstream ORF. Translation of the two ORFs seems to be independently controlled. This is in contrast to the picomaviruses with single ORF genomes, which are translated into a single polyprotein and post-translationally processed to give rise to both structural and non-structural proteins (Ruckert, 1996, In Fields et al., Eds., "Field Virology" Lippincoft-Raven, Philadelphia, Pa., pp. 609-654).

All picomaviruses that infect mammalian, insect, or plant hosts, contain a 5'-untranslated region. Like the IRES element in the intergenic region of insect picoma-like viruses with dicistronic genome, the 5' untranslated region of mammalian picornaviruses were shown to contain secondary structures that serve as an IRES element and thus, capable of cap-independent translation.

TABLE 1

Pair-wise comparisons of the intergenic regions of insect picorna-like viruses using the program MEGA.

|      | CrPV  | DCV   | PSIV  | HiPV  | TrV   | RhPV  | TSV   | BQCV  | ABPV  |
|------|-------|-------|-------|-------|-------|-------|-------|-------|-------|
| CrPV |       |       |       |       |       |       |       |       |       |
| DCV  | 0.200 |       |       |       |       |       |       |       |       |
| PSIV | 0.408 | 0.438 |       |       |       |       |       |       |       |
| HiPV | 0.385 | 0.446 | 0.331 |       |       |       |       |       |       |
| TrV  | 0.369 | 0.385 | 0.415 | 0.431 |       |       |       |       |       |
| RhPV | 0.369 | 0.369 | 0.462 | 0.485 | 0.346 |       |       |       |       |
| TSV  | 0.546 | 0.523 | 0.600 | 0.615 | 0.562 | 0.515 |       |       |       |
| BQCV | 0.292 | 0.323 | 0.400 | 0.446 | 0.392 | 0.415 | 0.562 |       |       |
| ABPV | 0.446 | 0.431 | 0.569 | 0.592 | 0.531 | 0.538 | 0.585 | 0.485 |       |

Example 2

Genome Organization of IHHNV

Figure 3:
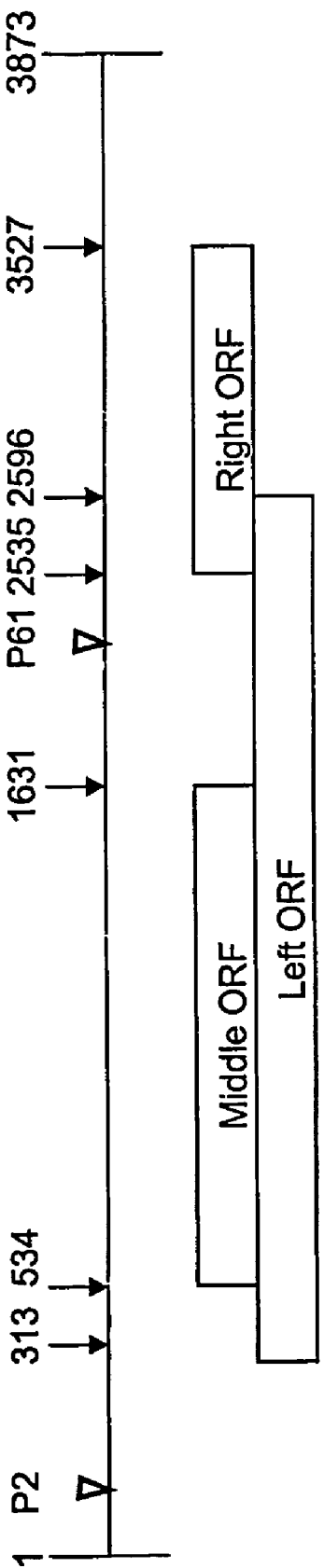

The IHHNV genome contains a single stranded linear DNA of 4.1 kb (Bonami et al., 1990). Almost the entire IHHNV genome except the 5'-and 3'-terminal ends has been sequenced (Shike et al., 2000, Virology, 277:167-177). There are three large open reading frames (ORFs) in the IHHNV genome (FIG. 3). The middle and the right ORFs are present in the plus 3 frame, whereas the left ORF is present in the plus 3 frame. The middle ORF completely overlaps with the left ORF, whereas the right ORF partially overlaps with the left ORF. The left, middle and the right ORFs have potential coding capacities of 666 amino acids (75.77 kDa), 363 aa (42.11 kDa) and 329 aa (37.48 kDa), respectively.

The left ORF most likely encodes for a major non-structural protein (NS-1), which contains replication initiation motifs, NTP-binding, and helicase domains. The right ORF encodes the capsid protein. The aa sequence of middle ORF does not show any similarity with database entries, and therefore, the putative function of this ORF is unknown. There are two potential promoters identified in IHHNV genome. One called P2 (based on map unit 2) is located upstream of the left ORF, and the other, called P61, is located upstream of right ORF (nucleotide position 2398-2448). Overall, the genome organization revealed that IHHNV is closely related to densoviruses of the genus *Brevidensovirus* in the family Parvoviridae (Shike et al., 2000, Virology, 277:167-177). A schematic representation of the genome organization of IHHNV genome is shown in FIG. 3.

Example 3

Amplification of IHHNV P61 Promoter by Polymerase Chain Reaction (PCR)

Figure 4:
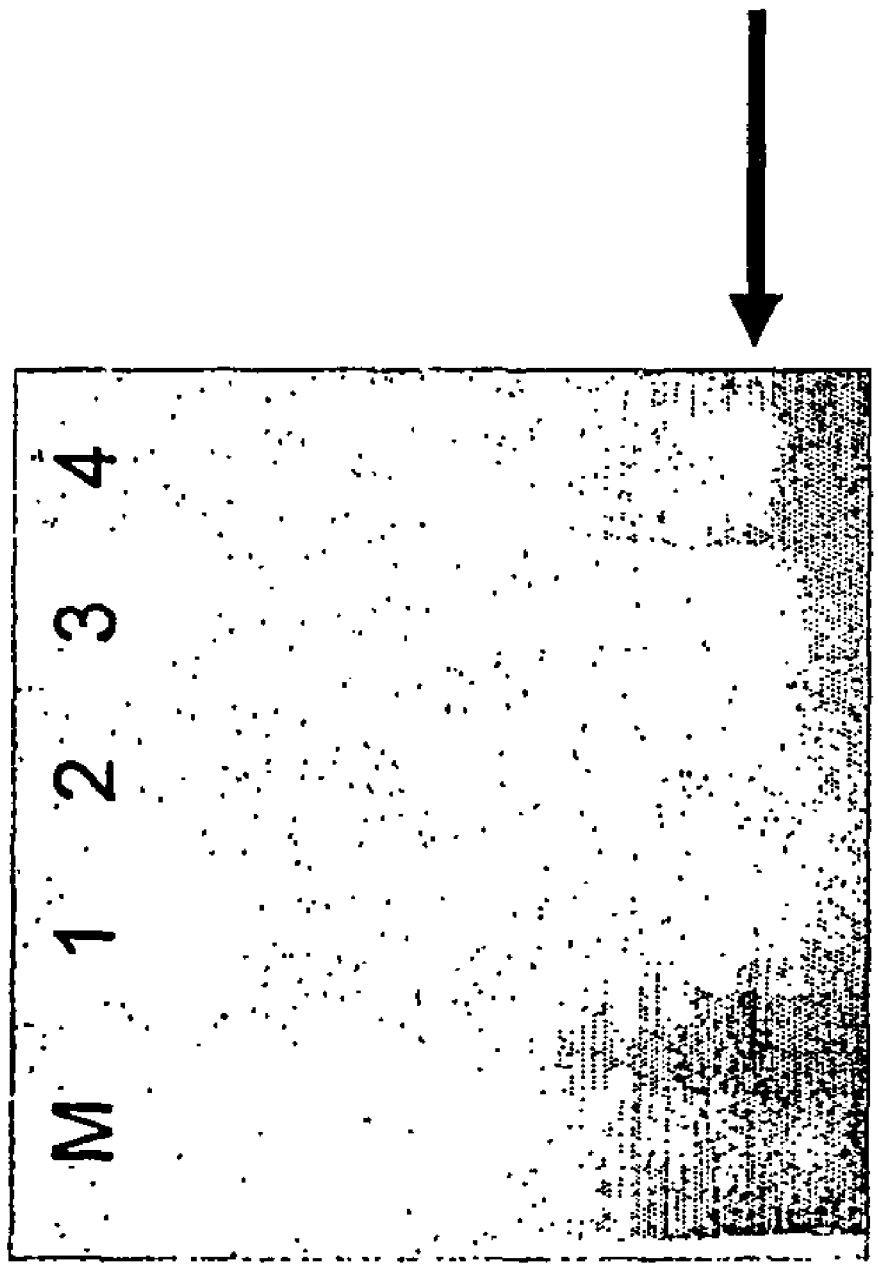

In order to evaluate the promoter activity of IHHNV P61 promoter, a 166 bp DNA flanking the P61 promoter was designed. The sequence of the primers were: IHHNP61F: 5'-GGTAC CTCCA GCTGA TGGTA AAGCT-3' (SEQ ID NO: 19; nucleotide position 2346-2371 in AF273215) and IHHNP61R: 5'-TTCGT ATTCT TGGAA GAGTC CTAG3" (SEQ ID NO: 20; nucleotide position 2488 in AF273215). The reaction mixture for the PCR included 1× Promega thermophilic DNA polymerase buffer, 2.0 millimolar $MgCl_2$, 0.4 micromolar dNTPs, 0.8 micromolar of forward and reverse primer, 7.5 units of Promega Taq DNA polymerase, and 100 nanograms of total genomic DNA isolated from IHHNV-infected shrimp in a 25 microliter reaction volume. The thermal profile for the PCR was 95 degrees Celsius for 5 minutes followed by 40 cycles of 95 degrees Celsius 30 seconds, 52 degrees Celsius 30 seconds, and 72 degrees Celsius 1 minute before cooling at 4 degrees Celsius. PCR amplified DNA was run in a 1.5% agarose gel containing ethidium bromide using Tris-acetate EDTA buffer and photographed. A photograph of the agarose gel is shown in FIG. 4. The amplified DNA was gel purified using Qiagen gel purification kit (Qiagen, California), and sequenced using IHHNVP61F primer. The nucleotide sequence of the amplified DNA showed 100% similarity with the GenBank database entry, AF273215.

Example 4

WSSV Genome Organization

Figure 5:
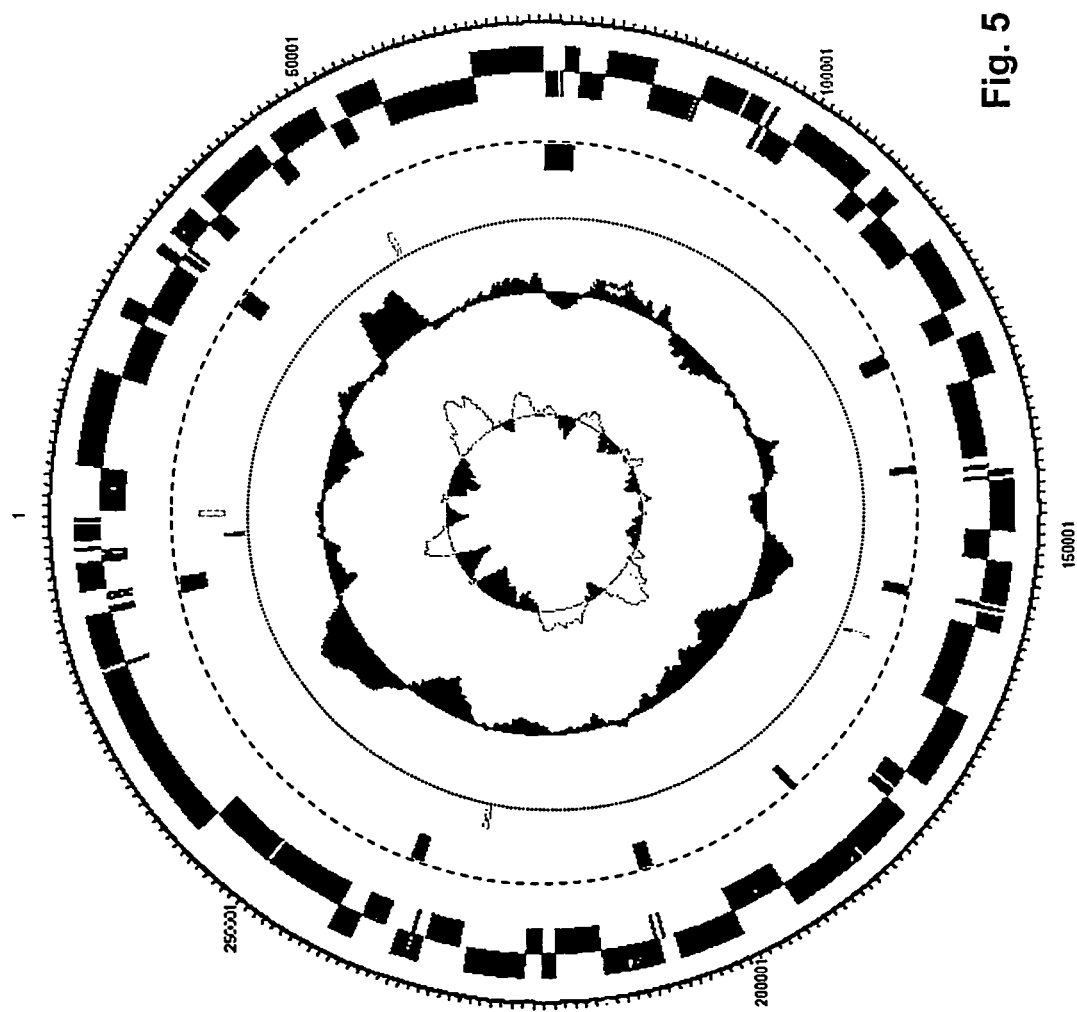

The genome of WSSV contains a circular double-stranded (ds) DNA of about 300 kb in size. So far three geographic isolates of WSSV have been completely sequenced including a Thai-isolate (292,967 bases, GenBank accession number AF369029, van Hulten et al., 2001, Virology 286:7-22), a Chinese isolate (305,307 bases, Yang et al., 2001, J. Virol. 75:11811-11820; GenBank accession number AF332093), and an isolate from Taiwan (307,287 bases, GenBank accession number AF440570). A representative genetic map of one of the isolates, Thai-isolate, is shown in FIG. 5. The three isolates show an overall nucleotide identity of 99.32% (Marks et al., 2004, Arch. Virol. 149:673-697). There are 181 to 184 predicted open reading frames (ORFs) in the WSSV genome depending on the isolates and only 6% of the ORFs have putative homologues among the GenBank database entries (van Hulten et al., 2001, Virology 286:7-22). The size differences among the isolates are due to a 13210 bp deletion in the Thai-isolate and a 1168 bp deletion in the WSSV Chinese isolate compared to the WSSV Taiwan isolate (Marks et al., 2004, Arch. Virol. 149:673-697).

WSV is morphologically similar to insect baculovirus. However, phylogenetic analysis of ribonucleotide reductase and protein kinase genes revealed that WSV does not share a common ancestor with baculoviruses (van Hulten et al., 2000, J. Gen. Virol. 81:307-316; van Hulten et al., 2001b, Virus Genes 22:201-207). Due to its limited sequence similarity with other viruses sequenced so far, WSSV has been placed in a new virus family, Nimaviridae, genus *Whispovirus*, as described in the art, for example in the NCBI's publicly-available web site relating to viral taxonomy.

Example 5

Transposable Elements in WSSV Genome

Figure 7:
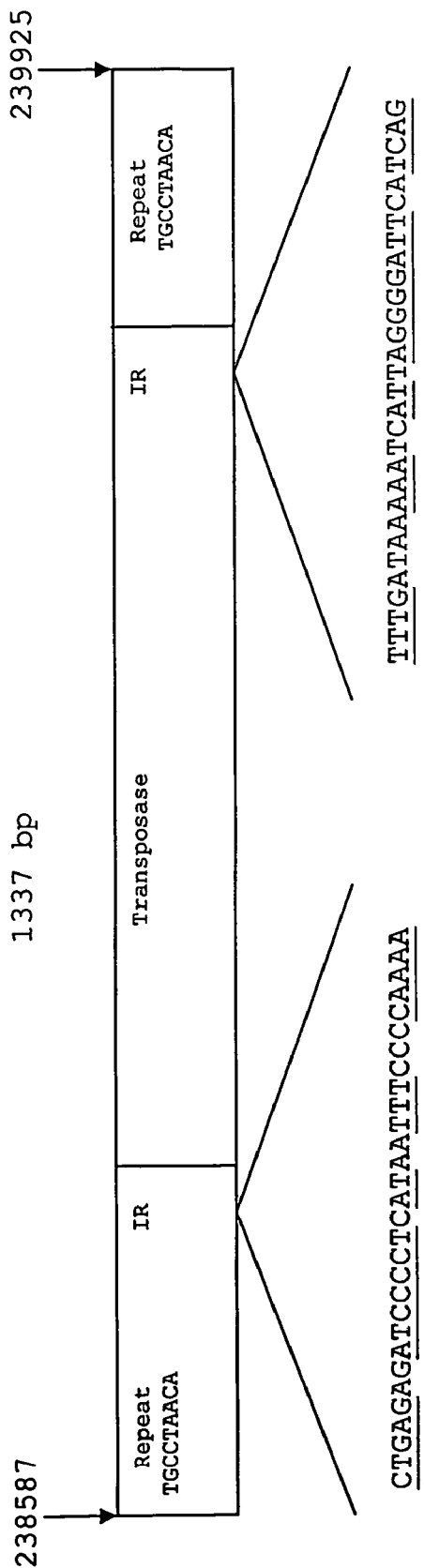

One of the three isolates of WSSV, the Taiwan isolate, contains a gene that encodes a transposase. The WSSV Taiwan isolate transposase gene shows 100% similarity with the homologous transposable elements of prokaryotic and eukaryotic origin. The regions upstream and the downstream of the ORF contains inverted repeats, a common feature of transposable elements. At the site of insertion of the transposable element in the WSSV genome, there has been a duplication of the WSSV sequence. The similarity of WSSV transposase with the homologous sequence in the GenBank database, and the genetic map of the transposase gene in WSSV genome are shown in FIGS. 6 and 7.

Example 6

Identification of a *Drosophila* Homologue of *Penelope* Transposable Element in Shrimp Transposable elements (TEs) have been identified from a wide variety of species including bacteria, plants, invertebrates, and vertebrates, and they constitute a considerable portion of the genetic makeup of a species. For example, TEs make up 3% of yeast genome (Kim et al., 1998), 10-15% of *Drosophila* sp. genome (SanMiguel et al., 1996, Science 274: 765-768), and about 50% of maize genome (Pimpinelli et al., 1995). In human, TEs constitute 43% of the genome representing 4.3 million TEs (Smit, 1999, Curr. Opin. Genet. Dev. 9:657-663; Li et al., 2001, Nature 409:847-849). Although TEs have long been held as "selfish DNA", only recently the importance of TEs is being realized (Kumar and Hirochika, 2001; Plasterk et al, 1999). TEs have been used in linkage mapping, genetic fingerprinting, molecular breeding, transgenic research, and evolutionary studies (Kumar et al., 2001, Trend Plant Biol. 6:127-134; Plasterk et al., 1999, Trends Genet.15:326-332).

Dhar and colleagues have recently reported the construction of a size fractionated genomic DNA library from shrimp (*Penaeus monodon*) for isolating microsatellite sequences for genetic analysis (Xu et al., 1999, Animal Genet. 30:1-7; Xu et al., 2004, J. Biochem. Genet., In press). GenBank database search for one of the DNA clones (GenBank accession number AF077579) showed significant similarity to a *Drosophila virilis* non-LTR transposable element *Penelope* (FIG. 8). The activation of *Penelope* elements in *Drosophila* has shown to be associated with a syndrome of aberrant traits collectively known as dysgenesis (Kidwell et al., 1997, Proc. Natl. Acad. Sci. USA 94:7704-7711). Intact *Penelope* elements of *Drosophila* encode a reverse transcriptase and an endonuclease of the UvrC type, which may play a role in *Penelope* integration (Lankenau et al., 1997, Proc. Natl. Acad. Sci. USA 94:196-201). Recently, Pyatkov et al. (2002, Proc. Natl. Acad. Sci. USA 99:16150-16155) used *Penelope* element as a transformation vector for germ-line transformation of *Drosophila*. *Penelope* was found to be actively transcribed, and undergoes massive copy number increase only in transformed lines where transformation was performed using a full-length copy as opposed to a truncated copy of the *Penelope* element.

Example 7

Construction of a Shrimp Transient Expression Vector

In order to construct a shrimp transient expression vector, IHHNV P61 promoter was amplified from IHHNV-infected shrimp using genomic DNA as template for the PCR (FIG. 4). The PCR amplified DNA showed 100% identity to IHHNV genomic sequence (GenBank accession number AF273215). The IHHNV P61 promoter is cloned into a TOPO vector following manufacturer's protocol (Invitrogen, Inc., California).

The entire TSV intergenic region between ORF1 and ORF2 is amplified by reverse transcriptase-polymerase chain reaction (RT-PCR) following published protocol (Dhar et al., 2002). The cDNA amplicon is cloned into TOPO vector (Invitrogen, Inc, California) and recombinant clones are sequenced to confirm the identity of the cDNA. The primer sequences for amplifying the TSV intergenic region are: Forward 5'-TAGCA CCACC CGATC GTAAA C-3' (SEQ ID NO: 21), Reverse 5'-TAATT AAGTC CCACC ACGCA AG-3' (SEQ ID NO: 22).

After confirming the sequence, the insert for the TSV intergenic region is digested from the recombinant clone with appropriate restriction enzyme, run in a 1.5% agarose gel following standard protocol (Sambrook et al., 1989, "Molecular Cloning: A laboratory manual" Ed. 2, Cold Spring Harbor Press, Cold Spring Harbor) and gel purified using the Qiagen gel purification kit (Qiagen, California).

The TSV intergenic region is cloned downstream of the IHHNV promoter. For this, the plasmid DNA from a recombinant clone containing the IHHNV promoter is digested with enzymes compatible with the TSV intergenic region insert and ligated using T4 DNA ligase and cloned in *E. coli* following standard protocol (Sambrook et al., 1989, "Molecular Cloning: A laboratory manual" Ed. 2, Cold Spring Harbor Press, Cold Spring Harbor).

Figure 9A:
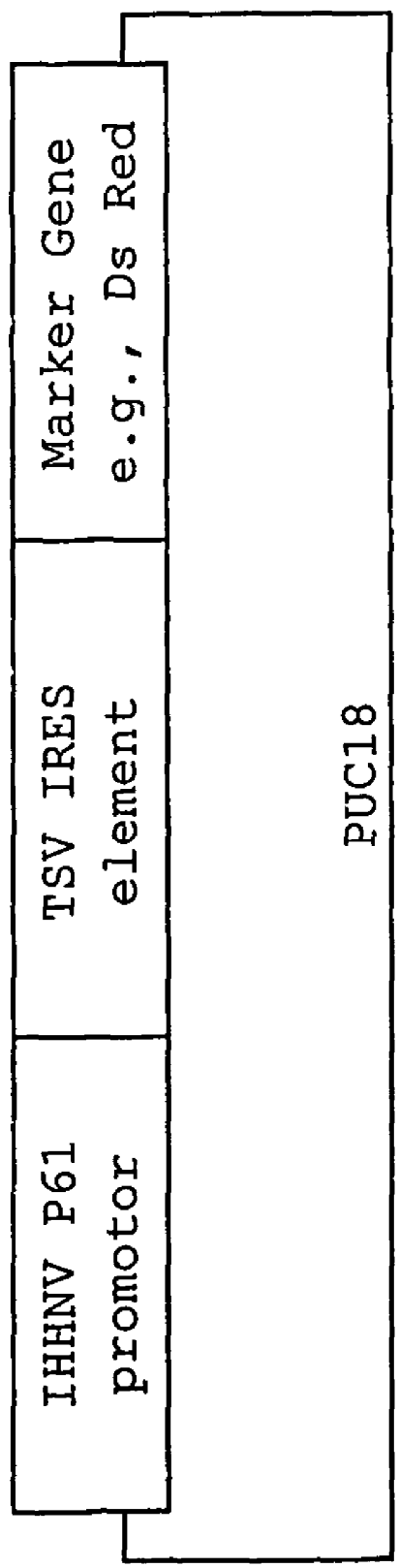

The recombinant clones containing the IHHNV P61 promoter and the TSV intergenic region are identified by colony PCR using IHHNVP61F primer and a vector derived primer. Clones that contain appropriate orientation (see FIG. 9A) are taken for subsequent sub-cloning into a pDsRed vector (BD Bioscience, California). The plasmid DNA containing the IHHNV P61 promoter and the TSV intergenic region are digested with appropriate enzyme, and cloned upstream of selectable marker DsRed in pDsRed vector (BDClontech). The plasmid DNA of the recombinant clones is sequenced to confirm the identity of the transformants. A schematic representation of shrimp transient vector is presented in FIG. 9A.

Example 8

Assay of Shrimp Transient Expression In Vivo

Plasmid DNA from recombinant shrimp expression vector is injected into the tail muscle of juvenile shrimp (about 1 gram) and the activity of the reporter gene (DsRed) is assayed either directly using a transilluminator and direct observation of the shrimp or by excision of the area injected and then extraction of soluble protein and analysis on a fluorescent microplate reader (Matz et al., 1999, Nat. Biotechnol. 17:969-973). Shrimp injected with the plasmid DNA of a non-recombinant clone serve as a control. Injected shrimp are sacrificed at 24, 48, 72 hr post injection and the levels of DsRed protein is measured. A fluorescent microplate reader is used for this analysis.

Tissue is homogenized with a tissue homogenizer in 50 millimolar Tris (pH 7.0) buffer plus proteinase inhibitor (1 millimolar phenylmethylsulfonyl fluoride, 5 millimolar benzamidine). The soluble portion is recovered after a brief centrifugation. This is analyzed for total protein by the Lowry method and aliquotted into black Nunc microplates in serial dilution. Fluorescence is read on SpectraFluor Plus (Tecan) reader at 485 nm excitation and 535 emissions. Controls are run with standard DsRed protein either made internally or obtained commercially.

Example 9

Assay of Shrimp Transient Expression In Vitro

Plasmid DNA from recombinant shrimp expression vector is injected to transfect primary cell culture of shrimp using lipofecting agent. Cells transfected with the plasmid DNA of non-recombinant clone serve as a control. The activity of the reporter gene (DsRed) is assayed at 24, 48, 72 hours post transfection following standard protocol (see Example 8).

Example 10

Cloning of a Full-Length Shrimp *Penelope* Element

In order to clone a full-length shrimp *Penelope* element, RT-PCR is performed using DNase treated total RNA from *Penaeus vannamei* shrimp to amplify a 500 bp amplicon using shrimp *Penelope* primers. The primers are designed based on the partial sequence of shrimp *Penelope* element available in the GenBank database (accession number AF077579). The RT-PCR protocol for amplifying the *Penelope* element is same as described for amplifying other shrimp genes like beta-actin (Dhar et al., 2002). The amplified cDNA is run in a 1.5% agarose gel following standard protocol (Sambrook et al., 1989, "Molecular Cloning: A laboratory manual" Ed. 2, Cold Spring Harbor Press, Cold Spring Harbor) and gel purified using Qiagen gel purification kit (Qiagen, California). The gel-purified cDNA is cloned in to a TOPO vector following manufacturer's recommendations (Invitrogen, Inc., California). Recombinant clones are sequenced to confirm the identity. The 500 bp partial clone of shrimp *Penelope* element is used as a probe to pull out a full-length clone of *Penelope* element from a shrimp (*Penaeus vannamei*) cDNA library (Dhar et al., 2004, "Comparison of expression profiles of healthy and white spot syndrome virus (WSSV) infected shrimp (*Penaeus vannamei*) by expressed sequence tag (EST) analysis," Presented at the World Aquaculture Society meeting, Shrimp Genomics Section, March 1-5, 2004, Honolulu, Hi.). If the isolated clone lacks 5'-end, 5'-RACE technique is employed to clone the 5'-terminal sequences following protocol used to clone the 5'-terminal sequence of other shrimp gene (Roux et al., 2002, J. Virol. 76:7140-7149). Recombinant clones are sequenced to confirm the identity of the clone.

Example 11

Construction of a Shrimp Transfection Vector Using a Shrimp *Penelope* Element In order to construct a transfection vector, IHHNV P61 promoter (FIG. 4) is cloned into TOPO vector following manufacturer's recommendations (Invitrogen, Inc., California). The entire shrimp *Penelope* element ORF is amplified from the recombinant clone by PCR. The primers for the PCR are based on the sequence of the *Penelope* element ORF. The primer sequences contain unique restriction enzyme sites that are need to clone it downstream of IHHNVP61 promoter. Amplified cDNA is digested with those enzymes before cloning downstream of IHHNVP61 promoter in TOPO vector. Ligation and transformation are done following standard protocol (Sambrook et al., 1989, "Molecular Cloning: A laboratory manual" Ed. 2, Cold Spring Harbor Press, Cold Spring Harbor).

The entire TSV intergenic region (TSV IRES) between ORF1 and ORF2 is amplified by reverse transcriptase-polymerase chain reaction (RT-PCR) following published protocol (Dhar et al., 2002, J. Virol. Meth. 104:69-82). The cDNA amplicon is cloned into TOPO vector (Invitrogen, Inc, California) and recombinant clones are sequenced to confirm the identity of the cDNA. The primer sequences for amplifying the TSV intergenic region are: Forward: 5'-TAGCACCACC CGATCGTAAA C-3' (SEQ ID NO: 23), Reverse 5'-TAAT-TAAGTC CCACCACGCA AG-3' (SEQ ID NO: 24). After confirming the sequence, the insert for TSV IRES is digested from the recombinant clone with appropriate restriction enzyme, run in a 1.5% agarose gel following standard protocol (Sambrook et al., 1989, "Molecular Cloning: A laboratory manual" Ed. 2, Cold Spring Harbor Press, Cold Spring Harbor) and gel purified using Qiagen gel purification kit (Qiagen, California). The TSV intergenic region is subcloned upstream of DsRed open reading frame in pDsRed vector (BD Bioscience, California). The recombinant clones containing the TSV intergenic region is sequenced to confirm the orientation and identity of the clones.

The TSV IRES-pDsRed plasmid is digested with two enzymes that cut upstream of the TSV IRES element. Similar enzymes are used to cut out the IHHNVP61-*Penelope* construct. The IHHNVP61-*Penelope* insert is gel purified using Qiagen gel purification kit before cloning upstream of the TSV intergenic region in pDsRed-TSV Intergenic construct. All enzyme digestion, ligation and transformation are done following standard protocol (Sambrook et al., 1989, "Molecular Cloning: A laboratory manual" Ed. 2, Cold Spring Harbor Press, Cold Spring Harbor). Recombinant clones are sequenced to confirm the orientation and identity of the inserts.

Figure 9B:
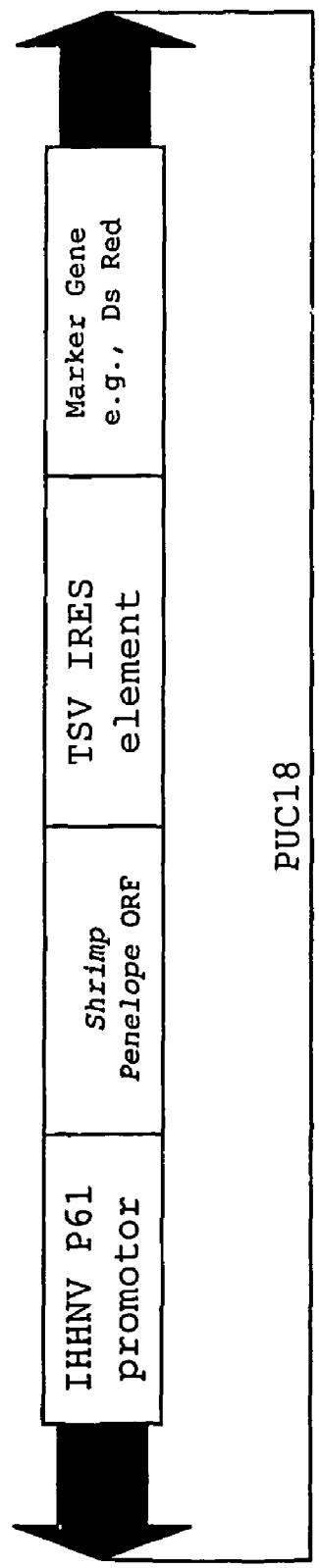

Finally, the inverted terminal repeat elements of shrimp *Penelope* are amplified from shrimp full-length *Penelope* gene and cloned upstream of IHHNVP61 promoter and downstream of the selectable maker gene (in this case DsRed). A schematic representation of the final shrimp transfection vector is presented in FIG. 9B.

Example 12

Construction of a Shrimp Transfection Vector Using a WSSV Transposable Element In order to construct a transfection vector, IHHNV P61 promoter (FIG. 4) is cloned into a TOPO vector following manufacturer's recommendations (Invitrogen, Inc., California). The entire shrimp WSSV transposase ORF is amplified by RT-PCR using DNase-treated total RNA from WSSV-infected shrimp tail muscle. The primers for the PCR are based on the sequence of the WSSV transposase ORF (GenBank accession number AF440570). The primer sequences contain unique restriction enzyme sites that are needed to clone it downstream of P61 promoter. Amplified cDNA is digested with those enzymes before cloning downstream of IHHNVP61 promoter in TOPO vector. Ligation and transformation are done following standard protocol (Sambrook et al., 1989, "Molecular Cloning: A laboratory manual" Ed. 2, Cold Spring Harbor Press, Cold Spring Harbor). Recombinant clones are sequenced to confirm the identity of the WSSV transposases clones.

The entire TSV intergenic region (including the TSV IRES) between ORF1 and ORF2 is amplified by reverse transcriptase-polymerase chain reaction (RT-PCR) following published protocol (Dhar et al., 2002, J. Virol. Meth. 104:69-82). The cDNA amplicon is cloned into a TOPO vector (Invitrogen, Inc, California) and recombinant clones are sequenced to confirm the identity of the cDNA. The primer sequences for amplifying the TSV intergenic region are: Forward: 5'-TAG-CACCACC CGATCGTAAA C-3' (SEQ ID NO: 25), Reverse 5'-TAATTAAGTC CCACCACGCA AG-3' (SEQ ID NO: 26). After confirming the sequence, the insert for TSV IRES is digested from the recombinant clone with appropriate restriction enzyme, run in a 1.5% agarose gel following standard protocol (Sambrook et al., 1989, "Molecular Cloning: A laboratory manual" Ed. 2, Cold Spring Harbor Press, Cold Spring Harbor) and gel purified using Qiagen gel purification kit (Qiagen, California). The TSV intergenic region is subcloned upstream of DsRed open reading frame in pDsRed vector (BD Bioscience, California). The recombinant clones containing the TSV intergenic region are sequenced to confirm the orientation and identity of the clones.

The TSV IRES-pDsRed plasmid is digested with two enzymes that cut upstream of the TSV IRES element. Similar enzymes are used to cut out the IHHNVP61-WSSV transposase construct. The IHNVP61-WSSV transposase is gel purified using Qiagen gel purification kit before cloning upstream of the TSV intergenic region in pDsRed-TSV Intergenic construct. All enzyme digestion, ligation and transformation are done following standard protocol (Sambrook et al., 1989, "Molecular Cloning: A laboratory manual" Ed. 2, Cold Spring Harbor Press, Cold Spring Harbor). Recombinant clones are sequenced to confirm the orientation and identity of the inserts.

Figure 10:
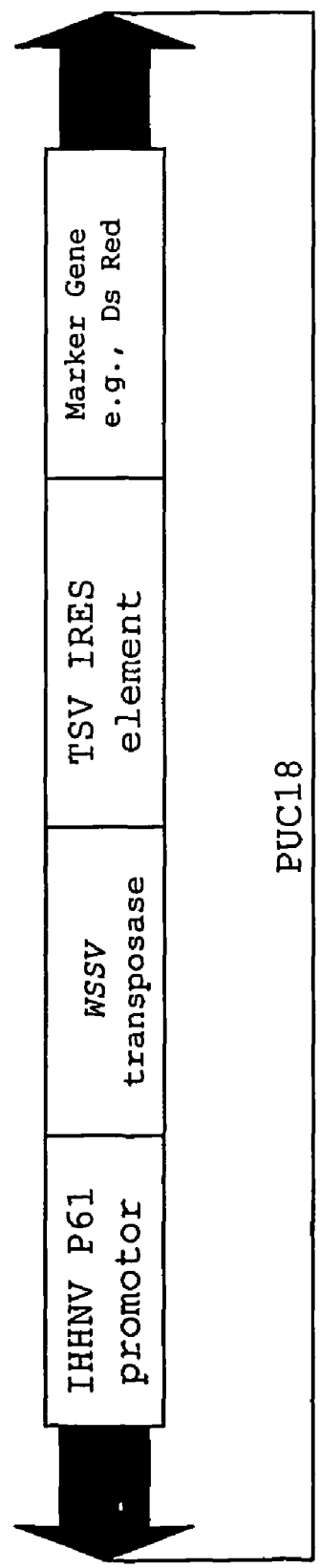

Finally, the inverted terminal repeat elements of WSSV are amplified by RT-PCR and cloned upstream of IHHNVP61 promoter and downstream of the selectable maker gene (in this case DsRed). A schematic representation of the final shrimp transfection vector is presented in FIG. 10.

Example 13

Transformation of shrimp primary cell culture with a transfection vector and assay of expression of recombinant protein in vitro Plasmid DNA from a recombinant shrimp transfection vector is used to transfect primary cell culture of shrimp using a lipofecting agent. Shrimp primary cell culture for hemocytes is made following a published protocol (e.g., Itami et al., 1999, Meth. Cell Sci. 21:237-244). Shrimp hemocyte primary culture is transfected with the plasmid DNA of shrimp transfection vector described in Example 11, FIG. 9B. The IHHNVP61 or P2 promoters driving Shrimp Penelope full-length ORF serve as a control. Alternative control promoters are available and are employed as needed (e.g., human cytomegaly virus (Tseng et al., 2000, Theriogenology 54:1421-1432) and pantropic retroviral promoters (Burns et al., 2000, PCT Publication WO00/75288; Shike et al., 2000, Virology, 277:167-177)). The activity of the reporter gene (DsRed) is assayed at 24, 48, 72 hours post transfection following the procedure outlined in Example 8.

In order to confirm the shrimp Penelope mediated integration of marker gene (DsRed), total genomic DNA is isolated from the shrimp transfected cells (primary cell lines) using Qiagen DNA extraction kit (Qiagen, California), digested with restriction enzymes, run in an agarose gel and blotted on to Nylon membrane (Sambrook et al., 1989, "Molecular Cloning: A laboratory manual" Ed. 2, Cold Spring Harbor Press, Cold Spring Harbor). Southern hybridization is performed using TSV IRES probe and DsRed probe (Sambrook et al., 1989, "Molecular Cloning: A laboratory manual" Ed. 2, Cold Spring Harbor Press, Cold Spring Harbor). Positive hybridization signals using these probes indicate transformation of the shrimp DNA with the transfection vector construct.

Example 14

Diagnostic Use of the Transgenic Cell Line of Example 13.

Adherent shrimp cells produced as in Example 13 are utilized for the diagnosis of viral disease by growth of the cells in a microplate. These cells are then exposed to shrimp tissue to be analyzed that has been macerated in a sterile tube and serially diluted using standard techniques. As infection proceeds, the fluorescence of the DsRed is monitored in a SpectraFluor Plus plate reader as described in Example 8. Cell mortality due to viral infection is reflected in a decrease in DsRed emission and viral titer can be determined rapidly versus a standard curve run simultaneously.

Example 15

Construction of a IHHNV p61 and p2 Promoter Driven Luciferase Vectors.

Figure 11:
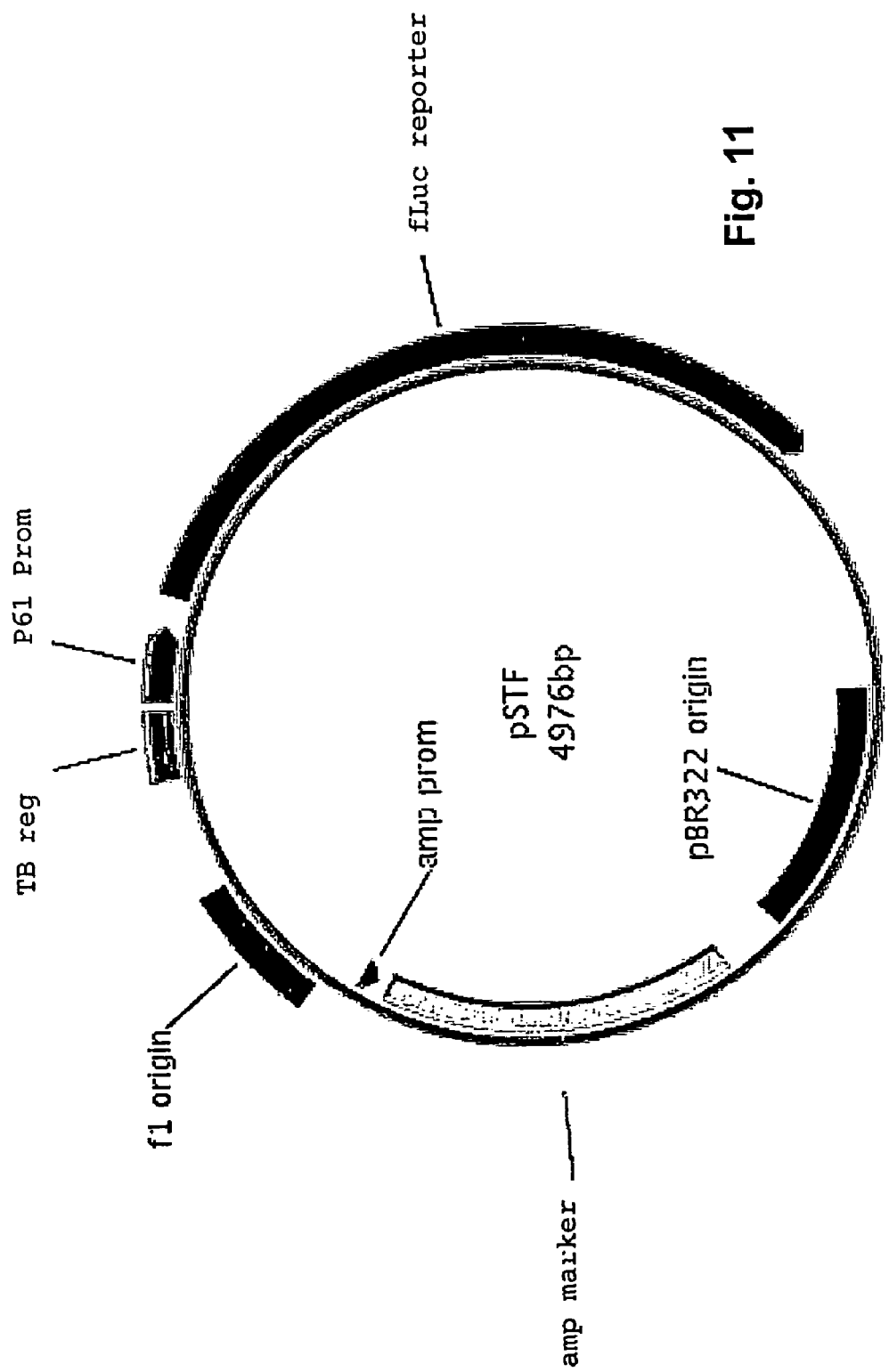
FIG. 11 is a map of a plasmid constructed by inserting the IHHNv p61 promoter into the pGL3-Basic vector (Promega).

The IHHNV p61 promoter element (GenBank accession # AF273215) was excised from a previously constructed and verified clone displayed in FIG. 11 using PlasMapper software (Dong et al., 2004, Nucl. Acids Res. 32(Web Server issue):W660-664).

Figure 12:
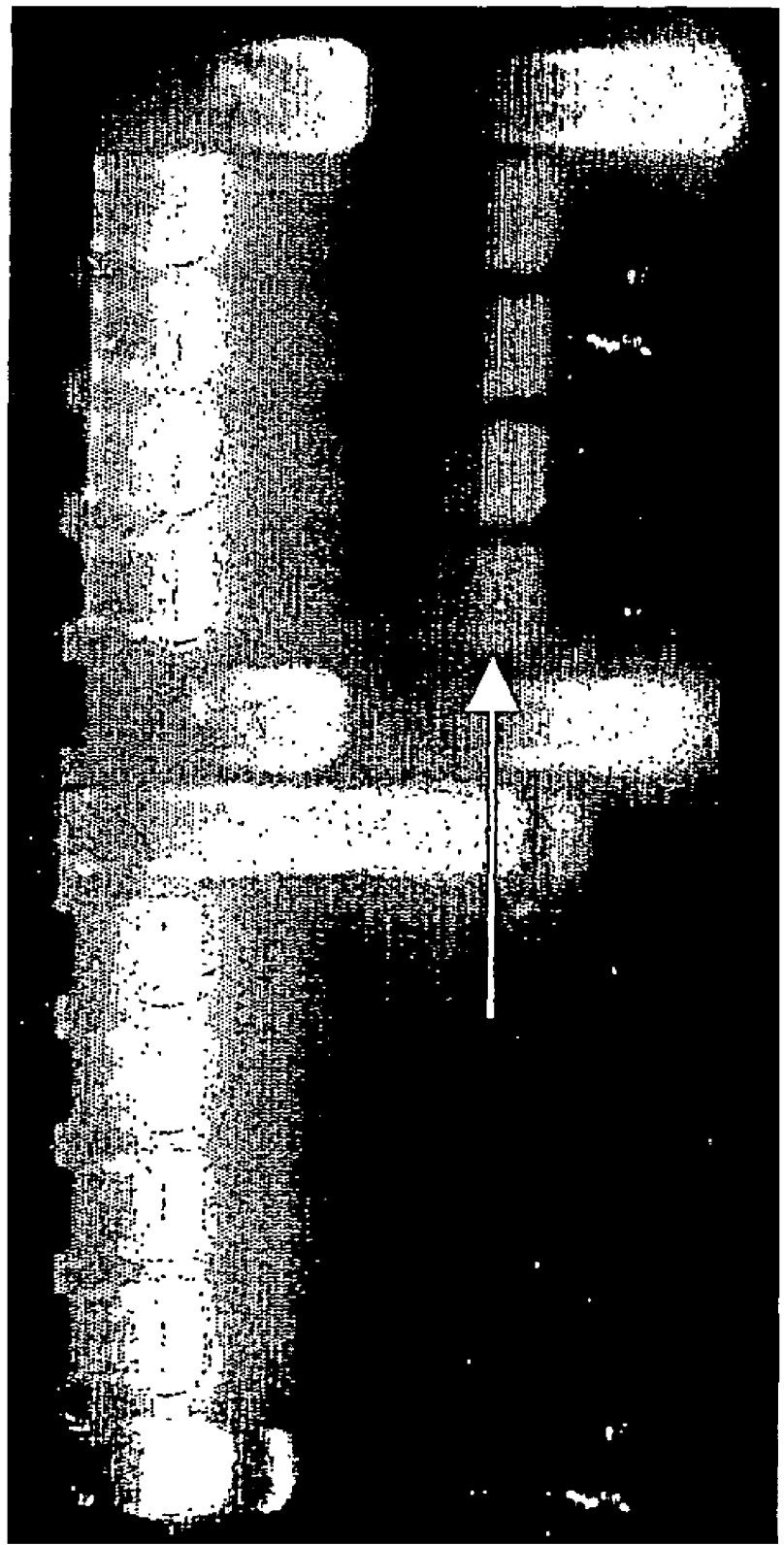
FIG. 12 is an image of an agarose gel separation of plasmids produced in Example 15 herein. Lane 1 contains a 1 kilobase DNA standard, Lanes 2-5 contain linearized pGL3 enhancer vector, Lane 6 contains a 100 base pair DNA standard, Lanes 7 & 8 contain 25 bp DNA standard, and Lanes 8-11 contain individual pSTF isolates double digested with SacI and NheI.

Briefly, the targeted fragment was PCR amplified using the forward primer p61 1 F (5'-TAC AGAGCTCGG TAC CTC CAG CTG A-3'; SEQ ID NO: 27) and the reverse primer p61 1 R (5'-GCT AGCTAGCTT CGT ATT CTT GGA AGA GTC-3'; SEQ ID NO: 28). This amplicon was then digested with SacI and NheI restriction enzymes (underlined in primer sequences) for insertion. The digested amplicon was gel purified using methods described for MiniElute Gel Extraction Kit in the manufacturer's instructions (Qiagen, Valencia, Calif.). The purified fragment was then inserted into a pGL3-Basic reporter vector containing a modified coding region for firefly (Photinus pyralis) luciferase (Promega Corp. Madison, Wis.) that had been digested and gel purified as above (FIG. 12).

Figure 13:
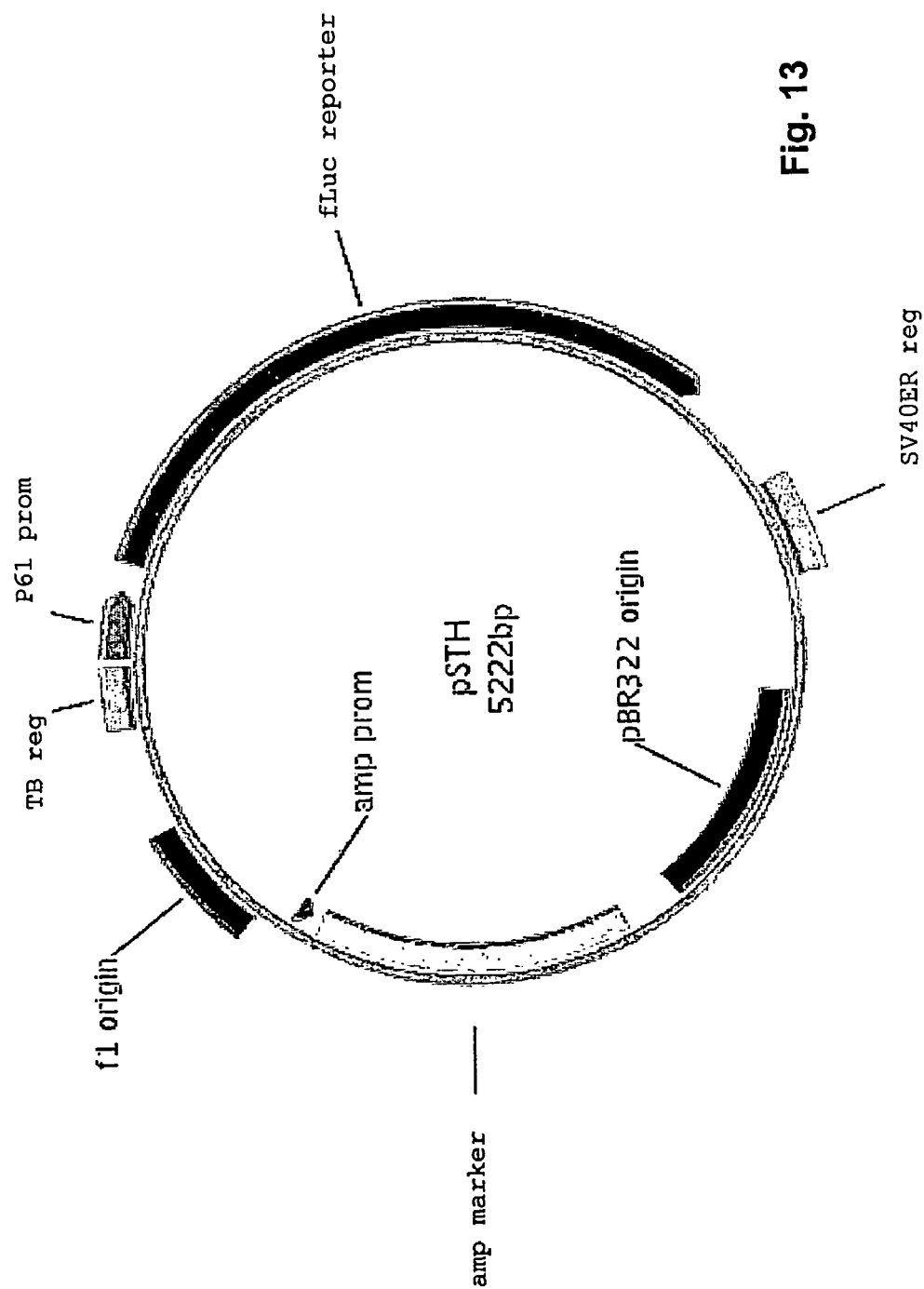
FIG. 13 is a map of a pSTH vector constructed using the IHHNV p61 promoter and the pGL3-Enhancer vector as a backbone.

Replicate clones were verified for sequence integrity at an off-site location using standard methods applied to an ABI 3100 capillary DNA analyzer (Applied Biosystems, Foster City, Calif.). The verified sequence was then excised out as before and inserted into the same location within a vector containing sequences reported to enhance expression of cloned fragments (pGL3-Enhancer, GenBank accession # U47297 (Cat# E1771, Promega Corp. Madison, Wis.). Again, replicate clones were verified as stated above. This produced the construct shown in FIG. 13.

Figure 14:
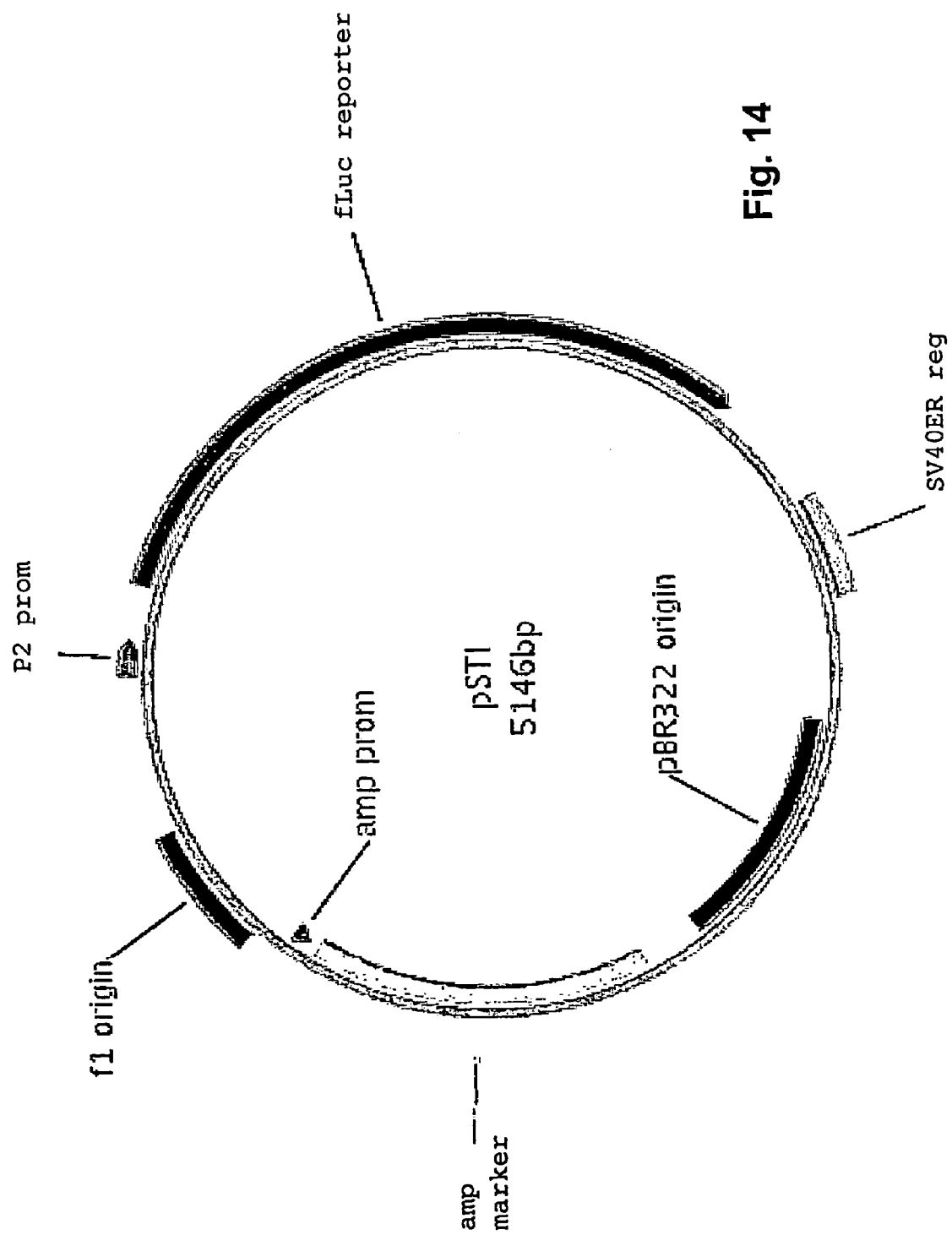
FIG. 14 is a map of a pSTI vector constructed using the IHHNV p2 promoter and the pGL3-Enhancer vector as a backbone.

The p2 promoter element from IHHNV was synthesized using methods described previously (Smith et al., 2003, Proc. Natl. Acad. Sci. USA 100:15440-15445) at a commercial facility. Briefly, the synthesized fragment was inserted into the general use cloning vector pUC19 (GenBank accession # L09137). That plasmid was then sequence verified at the same location. Using the synthesized SacI and NheI sequences for excision, the p2 fragment was removed and inserted into the pGL3-Enhancer vector mentioned above. Replicate clones were verified as above. This produced the construct shown in FIG. 14.

Example 16

Construction of IHHNV p2 and p61 Promoter Driven DsRed2 Reporter Plasmid Construction The IRES element from TSV (Cevallos et al., 2005, J. Virol. 79:677-683; GenBank accession # AF277675) was excised from a previously constructed and verified clone. Briefly, the targeted fragment was PCR amplified using the forward primer TSV IGR SACF (5'-GAT CGAGCTCTA GCA CCA CCC GAT CGT AAA C-3'; SEQ ID NO: 29) and TSV IGR BAMR (5'-GAT CGGATCCTA ATT AAG TCC CAC CAC-3'; SEQ ID NO: 30). This amplicon was then digested with SacI and BamHI restriction enzymes (underlined in primer sequences) for insertion. The digested amplicon was gel purified using standard methods. The purified fragment was then inserted into a previously constructed and verified reporter vector pSTD (FIG. 15A) containing a modified fluorescent protein to provide the construct shown in FIG. 15B. Replicate clones of the above were verified by sequencing.

An extended version of the TSV IGR was produced for cloning into the luciferase reporter vectors from above. The targeted fragment was PCR amplified using the forward primer TSV-IGR 2 F (5'-ATA CTCGAG AAC TAA TAG CAC CAC CCG-3'; SEQ ID NO: 31) and TSV-IGR 2 R (5'-TCC AAGCTT TTG TTG TAT CAA AAT TAT -3'; SEQ ID NO: 32), and electrophoresed in a 1.5% agarose gel (FIG. 16).

Example 17

Transient Expression of a Marker Protein in Shrimp.
Shrimp Handling.
Naive juvenile shrimp (*Penaeus vannamei*) free of specific pathogens were obtained from an outside source (*Penaeus (Litopenaeus) vannamei* (*Kona line*), about 1 gram, obtained from The Oceanic Institute. Waimanalo, Hi.). Specific Pathogen-Free (SPF) shrimp were free of those pathogens cited in Lightner (2003, "Exclusion of Specific Pathogens for Disease Prevention in a Penaeid Shrimp Biosecurity Program," In "Biosecurity in Aquaculture Production Systems: Exclusion of Pathogens and Other Undesirables" The World Aquaculture Society, Baton Rouge, La.). The animals were held in artificial seawater at about 26 degrees Celsius containing standard sea salt components (INSTANT OCEANS® Cat# SS1-160P, Aquarium Systems Inc., Mentor, Ohio) until use. Shrimp Grower feed (2.4 millimeter 3/32, Cat# SI-35, Zeigler Bros., Inc. Gardners, Pa.) was given at regular intervals with the amount being about 3% of the total body weight. Excess feces and uneaten food were aspirated from the tanks when needed.

Shrimp were then distributed into 5 liter tanks (STERILITE® SHOW OFFS™, UPC#073149894366, Sterilite Corp. Townsend, Mass.) containing 4 liters of artificial seawater as above. Each group (two groups of 6 and four groups of 7) was handled according to the procedures above until experiment termination.

DNA Injection.
Using a 1 milliliter syringe, 50 microliters of solution (20% Glycerol, 0.9% NaCl, about 10 micrograms of purified plasmid DNA) was injected just under the carapace into the tail muscle of the animals. The injection site of each animal was the same. Animals were sacrificed after about 72 hours and screened for the presence of luciferase.

Tissue Lysate.
Animals were removed from the tanks and chilled in ice-cold water for about 5 minutes to anesthetize them. The tissue surrounding the injection site was excised and placed into a tube of standard lysis reagent supplemented with components for stabilization (1× Cell Culture Lysis Reagent; Cat# E153A, Promega Corp., Madison, Wis. 1× Protease Inhibitor Cocktail; Cat# P-2714, Sigma, St. Louis, Mo.). The excised tissue was homogenized with a pestle (1.5 milliliter microcentrifuge tube pestles; Cat# 01-1415-5390, USA/Scientific Plastics®, Milton Keynes, England) to release total cellular protein content into solution. The samples were then clarified through centrifugation and the supernatant removed and placed in a clean tube. The samples were held at 4 degrees Celsius until use.

Luciferase Assay.
All reactions listed here were performed in microplate format (96-well, white bottom; Cat# 655083, Greiner bio-one, Inc., Longwood, Fla.) using standardized reagents (BRIGHT-GLO™ luciferase assay substrate; Cat# E263A, Promega Corp., Madison, Wis.) and the luminescent signal quantified using a luminometer (SPECTRAFluor PLUS; Firmware-V 6.00 06-07-2003 Spectra; XFLUOR4 Version-V 4.50, Tecan US. Research Triangle Park, N.C.). The default settings for the luminometer were used. All reactions were carried out in a total volume of 100 microliters (50 microliters of sample +50 microliters of standardized reagent). Readings were made as soon as possible after the addition of reagent.

A standard curve using recombinant luciferase (QUANTI-LUM® recombinant luciferase. Source: North American firefly, *Photinus pyralis*; Cat# E170B, Promega Corp. Madison, Wis.) was constructed beginning at a concentration of 1 femtogram per microliter and serially diluted 2-fold to 15.6 attograms per microliter. Duplicate wells were averaged together for producing the graph in FIG. 17.

Tissue lysate samples were read in triplicate wells. These technical replicate values were averaged together to form the chart in the data section below. Biological replicate values lying 1 standard deviation (SD) outside of the mean of the entire group were excluded. Standards were run to provide a plot of the standard curve values, shown in FIG. 17.

Macerated tissue samples were treated as described above and assayed for luciferase expression. Shrimp luciferase data were extrapolated into the luciferase standard curve (Table 2). Luciferase activity was expressed as relative light units (RLU) for each biological replicate in the experiment and normalized to the amount of tissue excised.

TABLE 2

Data from the luciferase assay comparing samples of shrimp tissue excised from tail muscle injected with controls (Buffer Only or Vector Only) or constructs containing IHHNV p2 promoter (pSTF1.1) or p61 promoter (pSTH). Underlined values indicate outliers (Defined as those samples that lie 1 standard deviation outside of the group mean).

| Treatments | RLU/100 mg Tissue |
|---|---|
| Buffer Only | 19.14 |
| Buffer Only | 31.67 |
| Buffer Only | 29.93 |
| Buffer Only | 6.62 |
| Buffer Only | 30.80 |
| Buffer Only | 13.95 |
| pSTF1.1 | 41.50 |
| pSTF1.1 | 42.26 |
| pSTF1.1 | 41.96 |
| pSTF1.1 | 33.09 |
| pSTF1.1 | 26.69 |
| pSTF1.1 | 57.86 |
| pSTF1.1 | 78.57 |
| pGL3-Enhancer | 45.98 |
| pGL3-Enhancer | 24.16 |
| pGL3-Enhancer | 13.42 |
| pGL3-Enhancer | 14.50 |
| pGL3-Enhancer | 32.56 |
| pGL3-Enhancer | 41.18 |
| pSTI1.1 | 411.49 |
| pSTI1.1 | 357.96 |
| pSTI1.1 | 25.00 |
| pSTI1.1 | 206.43 |
| pSTI1.1 | 166.81 |
| pSTI1.1 | 505.56 |
| pSTI1.1 | 222.54 |
| pSTH1.1 | 37.73 |
| pSTH1.1 | 20.81 |
| pSTH1.1 | 61.45 |
| pSTH1.1 | 14.42 |
| pSTH1.1 | 57.66 |
| pSTH1.1 | 119.09 |
| pSTH1.1 | 41.75 |

TABLE 3

Eliminating the outliers from Table 2 and calculating the mean, SD and % CV (% CV—Coefficient of Variation, defined as (SD/mean) * 100).

| Treatment | Mean | SD | % CV |
|---|---|---|---|
| Buffer Only | 27.88 | 5.87 | 21.06 |
| pSTF1.1 | 43.34 | 8.98 | 20.72 |
| pGL3-Enhancer | 32.63 | 8.51 | 26.08 |

TABLE 3-continued

Eliminating the outliers from Table 2 and calculating the mean, SD and % CV (% CV—Coefficient of Variation, defined as (SD/mean) * 100).

| Treatment | Mean | SD | % CV |
|---|---|---|---|
| pSTI1.1 | 222.54 | 105.66 | 47.48 |
| pSTH1.1 | 43.88 | 16.38 | 37.33 |

The disclosure of every patent, patent application, and publication cited herein is hereby incorporated herein by reference in its entirety.

While this invention has been disclosed with reference to specific embodiments, it is apparent that other embodiments and variations of this invention can be devised by others skilled in the art without departing from the true spirit and scope of the invention. The appended claims include all such embodiments and equivalent variations.

What is claimed is:

1. A non-naturally-occurring nucleic acid construct for expressing at least one cistron in a crustacean cell, the construct comprising a virus promoter from a virus that infects shrimp and an insect picornavirus (IPV) internal ribosome entry site (IRES), wherein the promoter and the IRES are operably linked with the at least one cistron for expression of the cistron in the cell, wherein the promoter is selected from the group consisting of P2 and P61 of infectious hypodermal and hematopoietic necrosis virus(IHHNV).

2. The construct of claim 1, wherein the IRES is capable of infecting crustaceans from the phylum Arthropoda.

3. The construct of claim 1, wherein the IRES is the IRES of an 5'-untranslated region of the insect picornavirus.

4. The construct of claim 1, wherein the IRES is the IRES of an intergenic region of the insect picornavirus having at least two ORFs.

5. The construct of claim 1, wherein the IRES is a Taura syndrome virus (TSV) IRES.

6. The construct of claim 5, wherein the IRES is the IRES of the 5'-untranslated region of TSV.

7. The construct of claim 1, wherein the IRES is an IRES of an IPV that infects shrimp.

8. The construct of claim 1, wherein the construct further comprises an animal cell origin of replication site (ORS).

9. The construct of claim 8, wherein the animal is a crustacean.

10. The construct of claim 9, wherein the crustacean is a shrimp.

11. The construct of claim 10, wherein the shrimp is a Penaeus shrimp.

12. The construct of claim 1, wherein the cistron comprises a first open reading frame (ORF).

13. The construct of claim 12, wherein the ORF is not interrupted by an intron.

14. The construct of claim 12, wherein the ORF encodes a detectable marker.

15. The construct of claim 12, further comprising a second ORF operably associated with the IRES.

16. The construct of claim 15, wherein at least one of the first and second ORFs encodes a protein not normally expressed in a shrimp.

17. A method of expressing a protein in a crustacean cell, the method comprising introducing into the cell a non-naturally-occurring nucleic acid construct, the construct comprising a viral promoter from a virus that infects a crustacean and an IPV IRES, wherein an ORF encoding the protein is operably linked with the promoter and the IRES, and wherein the promoter is selected from the group consisting of P2 and P61 of infectious hypodermal and hematopoietic necrosis virus (IHHNV); and culturing the cell for expression of the protein.

18. The method of claim 17, wherein the protein is a eukaryotic protein.

19. The method of claim 17, wherein the protein is a shrimp protein.

20. The method of claim 17, wherein the crustacean is a shrimp.

21. The method of claim 20, wherein the shrimp is a Penaeus shrimp.

22. The method of claim 17, wherein the construct is a plasmid.

23. The method of claim 17, wherein the construct is introduced into the cell using a virus vector.

24. The method of claim 17, wherein the construct is introduced into the cell ballistically.

25. The method of claim 17, wherein the construct is introduced into the cell by electroporation.

26. The method of claim 17, wherein the protein is a protein that exerts a protective effect on the cell.

27. The method of claim 17, wherein the protein is a protein that exerts a protective effect on an animal that comprises the cell.

28. The method of claim 17, wherein the protein is a protein that exerts a therapeutic effect on the cell.

29. The method of claim 17, wherein the protein is a protein that exerts a therapeutic effect on an animal that comprises the cell.

30. The method of claim 17, wherein the protein is a protein that exerts a regulatory effect on expression of an endogenous gene of the cell.

31. A method of expressing a protein in a marine animal cell, the method comprising introducing into the cell a non-naturally-occurring nucleic acid construct, the construct comprising a viral promoter from a virus that infects shrimp and an insect picornavirus IPV internal ribosome entry site IRES, wherein an ORF encoding the protein is operably linked with the promoter and the IRES for expression of the protein in a marine animal cell, and wherein the promoter is selected from the group consisting of P2 and P61 of infectious hypodermal and hematopoietic necrosis virus (IHHNV), and culturing the cell for expression of the protein.

32. A non-naturally-occurring nucleic acid construct for expressing a cistron in a crustacean cell, the construct comprising a virus promoter from a virus that infects crustacean and an insect picornavirus (IPV) internal ribosome entry site (IRES), wherein at least the promoter is operably linked to the cistron, wherein the IRES is from a virus known to infect the crustacean, wherein the promoter is selected from the group consisting of P2 and P61 of infectious hypodermal and hematopoietic necrosis virus(IHHNV).

33. A non-naturally-occurring nucleic acid construct for expressing at least one cistron in a host cell, the construct comprising a virus promoter and an insect picornavirus (IPV) internal ribosome entry site (IRES), wherein the promoter and the IRES are operably linked with the cistron for expression of the cistron in the host cell, wherein the promoter is selected from the group consisting of p2 and p61 of infectious hypodermal and hematopoietic necrosis virus (IHHNV) and wherein the host cell is selected from a group consisting of bacteria, yeast, insect, fish, shellfish and mollusk.

34. The construct of claim 33, wherein the IRES is the IRES of the 5'-untranslated region of a cricket paralysis-like picornavirus.

35. The construct of claim 33, wherein the cistron comprises at least one open reading frame (ORF).

36. The construct of claim 35, wherein the ORF encodes a protein not normally expressed in the host cell.

37. The construct of claim 36, wherein the protein is expressed in the host cell in vitro or in vivo.

38. The construct of claim 36, wherein the protein is antimicrobial or antiviral.

39. A non-naturally-occurring nucleic acid construct for expressing at least one cistron in a host cell, the construct comprising a virus promoter and an insect picornavirus (IPV) internal ribosome entry site (IRES), wherein the promoter and the IRES are operably linked with the cistron for expression of the cistron in the host cell, wherein the promoter is selected from the group consisting of p2 and p61 of infectious hypodermal and hematopoietic necrosis virus (IHHNV).

40. The construct of claim 39, wherein the host cell is selected from a group consisting of bacteria cell, yeast cell, insect cell, fish cell, shellfish cell, and animal cell.

* * * * *

SEQUENCE LISTING

```
<160> NUMBER OF SEQ ID NOS: 32

<210> SEQ ID NO 1
<211> LENGTH: 55
<212> TYPE: DNA
<213> ORGANISM: Cricket paralysis virus

<400> SEQUENCE: 1
agccctctct gcggtttttc agattaggta gtcgaaaaac ctaagaaatt tacct        55

<210> SEQ ID NO 2
<211> LENGTH: 55
<212> TYPE: DNA
<213> ORGANISM: Drosophila C virus

<400> SEQUENCE: 2
caccctctct gcttcttata tgattaggtt gtcatttaga ataagaaaat aacct        55

<210> SEQ ID NO 3
<211> LENGTH: 54
<212> TYPE: DNA
<213> ORGANISM: Plautia stali intestine virus

<400> SEQUENCE: 3
taccctcgtg ctcgctcaaa cattaagtgg tgttgtgcga aaagaatctc actt         54

<210> SEQ ID NO 4
<211> LENGTH: 54
<212> TYPE: DNA
<213> ORGANISM: Himetobi P virus

<400> SEQUENCE: 4
cacctaggtg cagccttgta gttttagtgg actttaggct aaagaatttc acta         54

<210> SEQ ID NO 5
<211> LENGTH: 50
<212> TYPE: DNA
<213> ORGANISM: black queen cell virus

<400> SEQUENCE: 5
gaactgtgct atgtttagaa gattaggtag tctctaaaca gaacaattta              50

<210> SEQ ID NO 6
<211> LENGTH: 51
<212> TYPE: DNA
<213> ORGANISM: triatoma virus

<400> SEQUENCE: 6
actgtacaga attttcctat acctcgagtc gggtttggaa tctaaggttg a            51

<210> SEQ ID NO 7
<211> LENGTH: 46
```

```
<212> TYPE: DNA
<213> ORGANISM: Rhopalosiphum padi virus

<400> SEQUENCE: 7
acgtcacagg agagcatacg ctaggtcgcg ttgactatcc ttatat            46

<210> SEQ ID NO 8
<211> LENGTH: 60
<212> TYPE: DNA
<213> ORGANISM: Taura syndrome virus

<400> SEQUENCE: 8
gaaagtccca gtcactttgg gcaaagtaga cagccgcgct tgcgtggtgg gacttaatta    60

<210> SEQ ID NO 9
<211> LENGTH: 43
<212> TYPE: DNA
<213> ORGANISM: acute bee paralysis virus

<400> SEQUENCE: 9
gataggaaca gctatattgg gtagttgtag cagttgtatt taa              43

<210> SEQ ID NO 10
<211> LENGTH: 402
<212> TYPE: PRT
<213> ORGANISM: white spot syndrome virus - Taiwan isolate

<400> SEQUENCE: 10
```

Met Cys Glu Leu Asp Ile Leu His Asp Ser Leu Tyr Gln Phe Cys Pro
1               5                   10                  15

Glu Leu His Leu Lys Arg Leu Asn Ser Leu Thr Leu Ala Cys His Ala
            20                  25                  30

Leu Leu Asp Cys Lys Thr Leu Thr Leu Thr Glu Leu Gly Arg Asn Leu
        35                  40                  45

Pro Thr Lys Ala Arg Thr Lys His Asn Ile Lys Arg Ile Asp Arg Leu
    50                  55                  60

Leu Gly Asn Arg His Leu His Lys Glu Arg Leu Ala Val Tyr Arg Trp
65                  70                  75                  80

His Ala Ser Phe Ile Cys Ser Gly Asn Thr Met Pro Ile Val Leu Val
                85                  90                  95

Asp Trp Ser Asp Ile Arg Glu Gln Lys Arg Leu Met Val Leu Arg Ala
            100                 105                 110

Ser Val Ala Leu His Gly Arg Ser Val Thr Leu Tyr Glu Lys Ala Phe
        115                 120                 125

Pro Leu Ser Glu Gln Cys Ser Lys Lys Ala His Asp Gln Phe Leu Ala
    130                 135                 140

Asp Leu Ala Ser Ile Leu Pro Ser Asn Thr Thr Pro Leu Ile Val Ser
145                 150                 155                 160

Asp Ala Gly Phe Lys Val Pro Trp Tyr Lys Ser Val Glu Lys Leu Gly
                165                 170                 175

Trp Tyr Trp Leu Ser Arg Val Arg Gly Lys Val Gln Tyr Ala Asp Leu
            180                 185                 190

Gly Ala Glu Asn Trp Lys Pro Ile Ser Asn Leu His Asp Met Ser Ser
        195                 200                 205

Ser His Ser Lys Thr Leu Gly Tyr Lys Arg Leu Thr Lys Ser Asn Pro
    210                 215                 220

Ile Ser Cys Gln Ile Leu Leu Tyr Lys Ser Arg Ser Lys Gly Arg Lys
225                 230                 235                 240

```
Asn Gln Arg Ser Thr Arg Thr His Cys His His Pro Ser Pro Lys Ile
                245                 250                 255

Tyr Ser Ala Ser Ala Lys Glu Pro Trp Ile Leu Ala Thr Asn Leu Pro
            260                 265                 270

Val Glu Ile Arg Thr Pro Lys Gln Leu Val Asn Ile Tyr Ser Lys Arg
        275                 280                 285

Met Gln Ile Glu Glu Thr Phe Arg Asp Leu Lys Ser Pro Ala Tyr Gly
    290                 295                 300

Leu Gly Leu Arg His Ser Arg Thr Ser Ser Glu Arg Phe Asp Ile
305                 310                 315                 320

Met Leu Leu Ile Ala Leu Met Leu Gln Leu Thr Cys Trp Leu Ala Gly
                325                 330                 335

Val His Ala Gln Lys Gln Gly Trp Asp Lys His Phe Gln Ala Asn Thr
            340                 345                 350

Val Arg Asn Arg Asn Val Leu Ser Thr Val Arg Leu Gly Met Glu Val
        355                 360                 365

Leu Arg His Ser Gly Tyr Thr Ile Thr Arg Glu Asp Ser Leu Val Ala
    370                 375                 380

Ala Thr Leu Leu Thr Gln Asn Leu Phe Thr His Gly Tyr Val Leu Gly
385                 390                 395                 400

Lys Leu

<210> SEQ ID NO 11
<211> LENGTH: 402
<212> TYPE: PRT
<213> ORGANISM: Salmonella enterica subspecies senterica serovar Typhi

<400> SEQUENCE: 11

Met Cys Glu Leu Asp Ile Leu His Asp Ser Leu Tyr Gln Phe Cys Pro
1               5                   10                  15

Glu Leu His Leu Lys Arg Leu Asn Ser Leu Thr Leu Ala Cys His Ala
            20                  25                  30

Leu Leu Asp Cys Lys Thr Leu Thr Leu Thr Glu Leu Gly Arg Asn Leu
        35                  40                  45

Pro Thr Lys Ala Arg Thr Lys His Asn Ile Lys Arg Ile Asp Arg Leu
    50                  55                  60

Leu Gly Asn Arg His Leu His Lys Glu Arg Leu Ala Val Tyr Arg Trp
65                  70                  75                  80

His Ala Ser Phe Ile Cys Ser Gly Asn Thr Met Pro Ile Val Leu Val
                85                  90                  95

Asp Trp Ser Asp Ile Arg Glu Gln Lys Arg Leu Met Val Leu Arg Ala
            100                 105                 110

Ser Val Ala Leu His Gly Arg Ser Val Thr Leu Tyr Glu Lys Ala Phe
        115                 120                 125

Pro Leu Ser Glu Gln Cys Ser Lys Lys Ala His Asp Gln Phe Leu Ala
    130                 135                 140

Asp Leu Ala Ser Ile Leu Pro Ser Asn Thr Thr Pro Leu Ile Val Ser
145                 150                 155                 160

Asp Ala Gly Phe Lys Val Pro Trp Tyr Lys Ser Val Glu Lys Leu Gly
                165                 170                 175

Trp Tyr Trp Leu Ser Arg Val Arg Gly Lys Val Gln Tyr Ala Asp Leu
            180                 185                 190

Gly Ala Glu Asn Trp Lys Pro Ile Ser Asn Leu His Asp Met Ser Ser
        195                 200                 205

Ser His Ser Lys Thr Leu Gly Tyr Lys Arg Leu Thr Lys Ser Asn Pro
```

```
                  210                 215                 220
Ile Ser Cys Gln Ile Leu Leu Tyr Lys Ser Arg Ser Lys Gly Arg Lys
225                 230                 235                 240

Asn Gln Arg Ser Thr Arg Thr His Cys His His Pro Ser Pro Lys Ile
                245                 250                 255

Tyr Ser Ala Ser Ala Lys Glu Pro Trp Ile Leu Ala Thr Asn Leu Pro
                260                 265                 270

Val Glu Ile Arg Thr Pro Lys Gln Leu Val Asn Ile Tyr Ser Lys Arg
                275                 280                 285

Met Gln Ile Glu Glu Thr Phe Arg Asp Leu Lys Ser Pro Ala Tyr Gly
290                 295                 300

Leu Gly Leu Arg His Ser Arg Thr Ser Ser Glu Arg Phe Asp Ile
305                 310                 315                 320

Met Leu Leu Ile Ala Leu Met Leu Gln Leu Thr Cys Trp Leu Ala Gly
                325                 330                 335

Val His Ala Gln Lys Gln Gly Trp Asp Lys His Phe Gln Ala Asn Thr
                340                 345                 350

Val Arg Asn Arg Asn Val Leu Ser Thr Val Arg Leu Gly Met Glu Val
                355                 360                 365

Leu Arg His Ser Gly Tyr Thr Ile Thr Arg Glu Asp Ser Leu Val Ala
370                 375                 380

Ala Thr Leu Leu Thr Gln Asn Leu Phe Thr His Gly Tyr Val Leu Gly
385                 390                 395                 400

Lys Leu

<210> SEQ ID NO 12
<211> LENGTH: 9
<212> TYPE: DNA
<213> ORGANISM: white spot syndrome virus - Taiwan isolate

<400> SEQUENCE: 12 tgcctaaca                                                                 9

<210> SEQ ID NO 13
<211> LENGTH: 30
<212> TYPE: DNA
<213> ORGANISM: white spot syndrome virus - Taiwan isolate

<400> SEQUENCE: 13
ctgagagatc ccctcataat ttccccaaaa                                         30

<210> SEQ ID NO 14
<211> LENGTH: 30
<212> TYPE: DNA
<213> ORGANISM: white spot syndrome virus - Taiwan isolate

<400> SEQUENCE: 14
tttgataaaa atcattaggg gattcatcag                                         30

<210> SEQ ID NO 15
<211> LENGTH: 144
<212> TYPE: PRT
<213> ORGANISM: Penaeus monodon

<400> SEQUENCE: 15

Leu Pro Thr Asn Val Phe Leu Gln Leu Ile Arg Leu Cys Val Glu Ser
1               5                  10                  15

Asn Phe Phe Ser Phe Glu Gly Arg Phe Tyr Ser Gln Thr Phe Gly Val
                20                  25                  30
```

```
Ala Met Gly Ser Pro Leu Tyr Pro Val Leu Ala Asn Leu Phe Met Glu
        35                  40                  45

Phe Phe Glu Ser Glu Leu Leu Pro Ser Ile Ser Leu Arg Pro Ser Val
    50                  55                  60

Trp Leu Arg Tyr Val Asp Asp Val Ala Leu Trp Pro His Asp Pro Ala
65                  70                  75                  80

Leu Phe Pro Asp Phe Leu Met Arg Leu Asn Ser Leu Ser Pro Ser Ile
                85                  90                  95

Arg Phe Lys Val Glu Trp Glu Val Asp Asn Lys Leu Pro Phe Leu Asp
            100                 105                 110

Thr Leu Val His Arg Ser Ala Glu His Phe Ser Phe Phe Ile Cys Arg
        115                 120                 125

Lys Pro Met His Ser Gly Met Tyr Ile Thr Leu Leu Ser Tyr His Pro
    130                 135                 140

<210> SEQ ID NO 16
<211> LENGTH: 144
<212> TYPE: PRT
<213> ORGANISM: Drosophila virilis

<400> SEQUENCE: 16

Ile Pro Lys Gln Leu Phe Met Asp Ile Val Arg Phe Cys Ile Glu Glu
1               5                   10                  15

Asn Arg Tyr Phe Lys Tyr Glu Asp Lys Ile Tyr Thr Gln Leu Lys Gly
            20                  25                  30

Met Pro Met Gly Ser Pro Ala Ser Pro Val Ile Ala Asp Ile Leu Met
        35                  40                  45

Glu Glu Leu Leu Asp Lys Ile Thr Asp Lys Leu Lys Ile Lys Pro Arg
    50                  55                  60

Leu Leu Thr Lys Tyr Val Asp Asp Leu Phe Ala Ile Thr Asn Lys Ile
65                  70                  75                  80

Asp Val Glu Asn Ile Leu Lys Glu Leu Asn Ser Phe His Lys Gln Ile
                85                  90                  95

Lys Phe Thr Met Glu Leu Glu Lys Asp Gly Lys Leu Pro Phe Leu Asp
            100                 105                 110

Ser Ile Val Ser Arg Met Asp Asn Thr Leu Lys Ile Lys Trp Tyr Arg
        115                 120                 125

Lys Pro Ile Ala Ser Gly Arg Ile Leu Asn Phe Asn Ser Asn His Pro
    130                 135                 140

<210> SEQ ID NO 17
<211> LENGTH: 12
<212> TYPE: PRT
<213> ORGANISM: Taura syndrome virus

<400> SEQUENCE: 17

Ala Asn Pro Val Glu Ile Asp Asn Phe Asp Thr Thr
1               5                   10

<210> SEQ ID NO 18
<211> LENGTH: 7
<212> TYPE: PRT
<213> ORGANISM: Taura syndrome virus

<400> SEQUENCE: 18

Met Pro Ala Asn Pro Val Glu
1               5
```

```
<210> SEQ ID NO 19
<211> LENGTH: 25
<212> TYPE: DNA
<213> ORGANISM: Artificial
<220> FEATURE:
<223> OTHER INFORMATION: Primer flanking the IHHNV P61 promoter

<400> SEQUENCE: 19
ggtacctcca gctgatggta aagct                                              25

<210> SEQ ID NO 20
<211> LENGTH: 24
<212> TYPE: DNA
<213> ORGANISM: Artificial
<220> FEATURE:
<223> OTHER INFORMATION: Primer flanking the IHHNV P61 promoter

<400> SEQUENCE: 20
ttcgtattct tggaagagtc ctag                                               24

<210> SEQ ID NO 21
<211> LENGTH: 21
<212> TYPE: DNA
<213> ORGANISM: Artificial
<220> FEATURE:
<223> OTHER INFORMATION: primer sequence for amplifying the TSV
      intergenic region

<400> SEQUENCE: 21
tagcaccacc cgatcgtaaa c                                                  21

<210> SEQ ID NO 22
<211> LENGTH: 22
<212> TYPE: DNA
<213> ORGANISM: Artificial
<220> FEATURE:
<223> OTHER INFORMATION: primer sequence for amplifying the TSV
      intergenic region

<400> SEQUENCE: 22
taattaagtc ccaccacgca ag                                                 22

<210> SEQ ID NO 23
<211> LENGTH: 21
<212> TYPE: DNA
<213> ORGANISM: Artificial
<220> FEATURE:
<223> OTHER INFORMATION: primer sequence for amplifying the TSV
      intergenic region

<400> SEQUENCE: 23
tagcaccacc cgatcgtaaa c                                                  21

<210> SEQ ID NO 24
<211> LENGTH: 22
<212> TYPE: DNA
<213> ORGANISM: Artificial
<220> FEATURE:
<223> OTHER INFORMATION: primer sequence for amplifying the TSV
      intergenic region

<400> SEQUENCE: 24
taattaagtc ccaccacgca ag                                                 22

<210> SEQ ID NO 25
<211> LENGTH: 21
<212> TYPE: DNA
<213> ORGANISM: Artificial
```

```
<220> FEATURE:
<223> OTHER INFORMATION: primer sequence for amplifying the TSV
      intergenic region

<400> SEQUENCE: 25
tagcaccacc cgatcgtaaa c                                            21

<210> SEQ ID NO 26
<211> LENGTH: 22
<212> TYPE: DNA
<213> ORGANISM: Artificial
<220> FEATURE:
<223> OTHER INFORMATION: primer sequence for amplifying the TSV
      intergenic region

<400> SEQUENCE: 26
taattaagtc ccaccacgca ag                                           22

<210> SEQ ID NO 27
<211> LENGTH: 24
<212> TYPE: DNA
<213> ORGANISM: Artificial
<220> FEATURE:
<223> OTHER INFORMATION: forward primer for amplification of p61 1 F
      fragment

<400> SEQUENCE: 27
tacagagctc ggtacctcca gctg                                         24

<210> SEQ ID NO 28
<211> LENGTH: 30
<212> TYPE: DNA
<213> ORGANISM: Artificial
<220> FEATURE:
<223> OTHER INFORMATION: reverse primer for amplification of p61 1 R
      fragment

<400> SEQUENCE: 28
gctagctagc ttcgtattct tggaagagtc                                   30

<210> SEQ ID NO 29
<211> LENGTH: 31
<212> TYPE: DNA
<213> ORGANISM: Artificial
<220> FEATURE:
<223> OTHER INFORMATION: forward primer TSV IGR SACF

<400> SEQUENCE: 29
gatcgagctc tagcaccacc cgatcgtaaa c                                 31

<210> SEQ ID NO 30
<211> LENGTH: 27
<212> TYPE: DNA
<213> ORGANISM: Artificial
<220> FEATURE:
<223> OTHER INFORMATION: reverse primer TSV IGR BAMR

<400> SEQUENCE: 30
gatcggatcc taattaagtc ccaccac                                      27

<210> SEQ ID NO 31
<211> LENGTH: 27
<212> TYPE: DNA
<213> ORGANISM: Artificial
<220> FEATURE:
<223> OTHER INFORMATION: forward primer TSV-IGR 2 F

<400> SEQUENCE: 31
```

```
atactcgaga actaatagca ccacccg                                        27

<210> SEQ ID NO 32
<211> LENGTH: 27
<212> TYPE: DNA
<213> ORGANISM: Artificial
<220> FEATURE:
<223> OTHER INFORMATION: reverse primer TSV-IGR 2 R

<400> SEQUENCE: 32
tccaagcttt tgttgtatca aaattat                                        27
```